(12) United States Patent
Park

(10) Patent No.: US 10,759,835 B2
(45) Date of Patent: Sep. 1, 2020

(54) MONOMERIC STREPTAVIDIN MUTANTS, METHODS OF USING THE SAME AND PROCESSES OF MANUFACTURING PROTEINS

(71) Applicant: The Research Foundation for The State University of New York, Buffalo, NY (US)

(72) Inventor: Sheldon Park, Amherst, NY (US)

(73) Assignee: The Research Foundation for The State University of New York, Amherst, NY (US)

(*) Notice: Subject to any disclaimer, the term of this patent is extended or adjusted under 35 U.S.C. 154(b) by 27 days.

(21) Appl. No.: 16/319,744

(22) PCT Filed: Jul. 25, 2017

(86) PCT No.: PCT/US2017/043724
§ 371 (c)(1),
(2) Date: Jan. 22, 2019

(87) PCT Pub. No.: WO2018/022618
PCT Pub. Date: Feb. 1, 2018

(65) Prior Publication Data
US 2019/0263872 A1    Aug. 29, 2019

Related U.S. Application Data

(60) Provisional application No. 62/366,241, filed on Jul. 25, 2016.

(51) Int. Cl.
C07K 14/36     (2006.01)
C07K 14/00     (2006.01)
C07K 14/195    (2006.01)

(52) U.S. Cl.
CPC .............. *C07K 14/36* (2013.01); *C07K 14/00* (2013.01); *C07K 14/195* (2013.01); *C07K 2319/00* (2013.01)

(58) Field of Classification Search
None
See application file for complete search history.

(56) References Cited

FOREIGN PATENT DOCUMENTS

WO    2010/129265 A2    11/2010
WO    2016/112921 A1    4/2016

OTHER PUBLICATIONS

Lim, K.H., et al., Stable, High-Affinity Streptavidin Monomer for Protein Labeling and Monovalent Biotin Detection, Biotechnol Bioeng, Jan. 2013, vol. 110, No. 1, pp. 57-67.

De Monte, D., et al., Expression and purification of soluble monomeric streptavidin in *Escherichia coli*, Appl Microbiol Biotechnol, 2014, vol. 98, No. 14, pp. 6285-6295.

GenPept Accession No. PDB:4JNJ_A: Chain A, Structure Based Engineering of Streptavidin Monomer with a Reduced Biotin Dissociation Rate, Nov. 13, 2013. //www.ncbi.nlm.nih.gov/protein/4JNJ_A.

Dundas, C.M., et al., Streptavidin-biotin technology: improvements and innovations in chemical and biological applications, Applied Microbiology and Biotechnology, Sep. 22, 2013, vol. 97, No. 21, pp. 9343-9353.

*Primary Examiner* — Anand U Desai
(74) *Attorney, Agent, or Firm* — Hodgson Russ LLP

(57) ABSTRACT

This disclosure provides streptavidin monomers that bind biotin with high affinity and which possess slow dissociation rates. The disclosure also provides methods of making and using those monomers.

20 Claims, 9 Drawing Sheets
Specification includes a Sequence Listing.

a.

```
              20        30        40         50         60
               |         |         |          |          |
wtSA   AEAGITGTWYNQLGSTFIVTAGADGALTGTYESAV--GNAES-RYVLTGRY
mSA    AEAGITGTWYNQSGSTFTVTAGADGNLTGQYENRAQGTGCQNSPYTLTGRY
Brad2  QGLPAPSYWKNERGSELLIWSANSGTIQGTFTNHAQGFACQGIPYPAAGSV 70        80        90       100       110
                 |         |         |         |         |
wtSA   DSAPATDGSGTALGWTVAWKNNYRNAHSATTWSGQYVGGAEARINTQWLLT
mSA    N--------GTKLEWRVEWNNSTENCHSRTEWRGQYQGGAEARINTQWNLT
Brad2  SP--------TGL----YFVVTFAQCNSFTRWVGTIKGS---QMPTSWTLF 120       130
               |         |
wtSA   SGTTEANAWKSTLVGHDTFTKVKPSAAS
mSA    YEGG---SGPATEQGQDTFTKVKPSAAS
Brad2  YVDNK--GKPSRLKGGDIFTRVW
``` b.

MKKTAIAIAVALAGFATVAQA-<u>TS</u>-HHHHHH-<u>EF</u>-<u>AS</u>-AEAGIT…PSAAS-<u>GS</u>-DYKDDDDK

OmpA 6xHis mSA FLAG

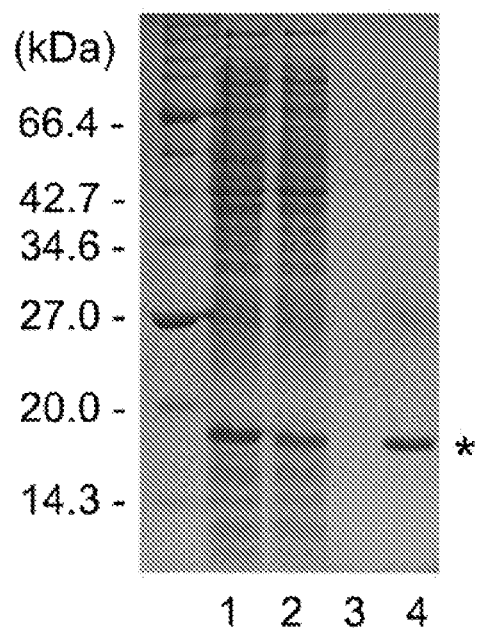
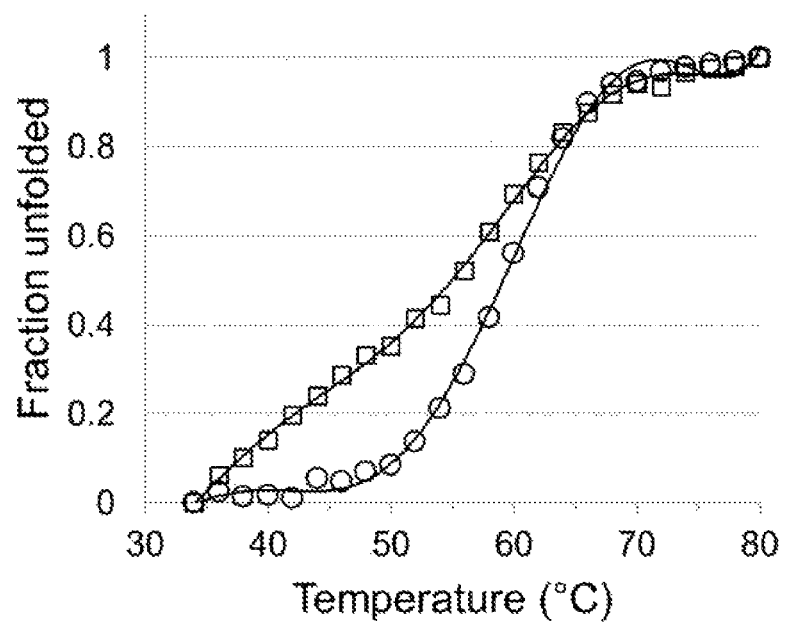
Figure 9

SEQUENCE LISTING

```
<160> NUMBER OF SEQ ID NOS: 22

<210> SEQ ID NO 1
<211> LENGTH: 119
<212> TYPE: PRT
<213> ORGANISM: artificial sequence
<220> FEATURE:
<223> OTHER INFORMATION: monomeric streptavidin

<400> SEQUENCE: 1

Ala Glu Ala Gly Ile Thr Gly Thr Trp Tyr Asn Gln Ser Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
            85                  90                  95

Gly Gly Ser Gly Pro Ala Thr Glu Gln Gly Gln Asp Thr Phe Thr Lys
            100                 105                 110

Val Lys Pro Ser Ala Ala Ser
```

```
<210> SEQ ID NO 2
<211> LENGTH: 119
<212> TYPE: PRT
<213> ORGANISM: artificial sequence
<220> FEATURE:
<223> OTHER INFORMATION: Modified streptavidin

<400> SEQUENCE: 2

Ala Glu Ala Gly Ile Thr Gly Thr Trp Tyr Asn Gln Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
        115

<210> SEQ ID NO 3
<211> LENGTH: 119
<212> TYPE: PRT
<213> ORGANISM: artificial sequence
<220> FEATURE:
<223> OTHER INFORMATION: Modified streptavidin

<400> SEQUENCE: 3

Ala Glu Ala Gly Ile Thr Gly Thr Trp Tyr Asn Gln Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Phe Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
        115

<210> SEQ ID NO 4
<211> LENGTH: 119
<212> TYPE: PRT
<213> ORGANISM: artificial sequence
<220> FEATURE:
<223> OTHER INFORMATION: Modified streptavidin

<400> SEQUENCE: 4
```

```
Ala Glu Ala Gly Ile Thr Gly Thr Trp Tyr Asn Gln Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Trp Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Thr Gln Gly Gln Asp Thr Phe Thr Lys
            100                 105                 110

Val Lys Pro Ser Ala Ala Ser
        115
```

<210> SEQ ID NO 5
<211> LENGTH: 119
<212> TYPE: PRT
<213> ORGANISM: artificial sequence
<220> FEATURE:
<223> OTHER INFORMATION: Modified streptavidin

<400> SEQUENCE: 5

```
Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
        115
```

<210> SEQ ID NO 6
<211> LENGTH: 119
<212> TYPE: PRT
<213> ORGANISM: artificial sequence
<220> FEATURE:
<223> OTHER INFORMATION: Modified streptavidin

<400> SEQUENCE: 6

```
Ala Glu Ala Gly Ile Thr Gly Thr Trp Tyr Asn Glu Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
```

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
            115

<210> SEQ ID NO 7
<211> LENGTH: 119
<212> TYPE: PRT
<213> ORGANISM: artificial sequence
<220> FEATURE:
<223> OTHER INFORMATION: modified streptavidin

<400> SEQUENCE: 7

Ala Glu Ala Gly Ile Thr Gly Thr Trp Tyr Asn Asp Arg Gly Ser Thr
1               5                   10                  15

Phe Thr Val Thr Ala Gly Ala Asp Gly Asn Leu Thr Gly Gln Tyr Glu
                20                  25                  30

Asn Arg Ala Gln Gly Thr Gly Cys Gln Asn Ser Pro Tyr Thr Leu Thr
            35                  40                  45

Gly Arg Tyr Asn Gly Thr Lys Leu Glu Trp Arg Val Glu Trp Asn Asn
        50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
            115

<210> SEQ ID NO 8
<211> LENGTH: 119
<212> TYPE: PRT
<213> ORGANISM: artificial sequence
<220> FEATURE:
<223> OTHER INFORMATION: Modified streptavidin

<400> SEQUENCE: 8

Ala Glu Ala Gly Ile Thr Gly Thr Trp Tyr Asn Glu Arg Gly Ser Thr
1               5                   10                  15

Phe Thr Val Thr Ala Gly Ala Asp Gly Asn Leu Thr Gly Gln Tyr Glu
                20                  25                  30

Asn Arg Ala Gln Gly Phe Gly Cys Gln Asn Ser Pro Tyr Thr Leu Thr
            35                  40                  45

Gly Arg Tyr Asn Gly Thr Lys Leu Glu Trp Arg Val Glu Trp Asn Asn
        50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
        115

<210> SEQ ID NO 9
<211> LENGTH: 119
<212> TYPE: PRT
<213> ORGANISM: artificial sequence
<220> FEATURE:
<223> OTHER INFORMATION: Modified streptavidin

<400> SEQUENCE: 9

Ala Glu Ala Gly Ile Thr Gly Thr Trp Tyr Asn Asp Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Phe Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Pro Ser Ala Ala Ser
        115

<210> SEQ ID NO 10
<211> LENGTH: 119
<212> TYPE: PRT
<213> ORGANISM: artificial sequence
<220> FEATURE:
<223> OTHER INFORMATION: Modified streptavidin

<400> SEQUENCE: 10

Ala Glu Ala Gly Ile Thr Gly Thr Trp Tyr Asn Glu Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Trp Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Thr Gln Gly Gln Asp Thr Phe Thr Lys
            100                 105                 110

Val Lys Pro Ser Ala Ala Ser
        115

<210> SEQ ID NO 11
<211> LENGTH: 119
<212> TYPE: PRT
<213> ORGANISM: artificial sequence
<220> FEATURE:
<223> OTHER INFORMATION: Modified streptavidin

<400> SEQUENCE: 11

Ala Glu Ala Gly Ile Thr Gly Thr Trp Tyr Asn Asp Arg Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Trp Gly Cys Gln Asn Ser Pro Tyr Thr Leu Thr
        35                  40                  45

Gly Arg Tyr Asn Gly Thr Lys Leu Glu Trp Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Thr Gln Gly Gln Asp Thr Phe Thr Lys
            100                 105                 110

Val Lys Pro Ser Ala Ala Ser
        115

<210> SEQ ID NO 12
<211> LENGTH: 21
<212> TYPE: PRT
<213> ORGANISM: artificial sequence
<220> FEATURE:
<223> OTHER INFORMATION: Recombinant signal peptide

<400> SEQUENCE: 12

Met Lys Lys Thr Ala Ile Ala Ile Ala Val Ala Leu Ala Gly Phe Ala
1               5                   10                  15

Thr Val Ala Gln Ala
            20

<210> SEQ ID NO 13
<211> LENGTH: 8
<212> TYPE: PRT
<213> ORGANISM: artificial sequence
<220> FEATURE:
<223> OTHER INFORMATION: Recombinant FLAG epitope

<400> SEQUENCE: 13

Asp Tyr Lys Asp Asp Asp Asp Lys
1               5

<210> SEQ ID NO 14
<211> LENGTH: 54
<212> TYPE: PRT
<213> ORGANISM: artificial sequence
<220> FEATURE:
<223> OTHER INFORMATION: A combination of FLAG and cMyc tags

<400> SEQUENCE: 14

Gly Ser Asp Ala Lys Asp Arg Ser Asp Lys Gly Ser Glu Gln Lys Leu
1               5                   10                  15

Ile Ser Glu Glu Asp Leu Gly Ser Asp Ala Lys Asp Ser Ala Asp Lys
            20                  25                  30

Gly Ser Glu Gln Lys Leu Ile Ser Glu Ala Arg Lys Gly Ser Asp Tyr
        35                  40                  45

Lys Asp Asp Asp Asp Lys
    50

<210> SEQ ID NO 15

```
<211> LENGTH: 5
<212> TYPE: PRT
<213> ORGANISM: artificial sequence
<220> FEATURE:
<223> OTHER INFORMATION: Synthetic peptide

<400> SEQUENCE: 15

Gly Gly Ser Gly Lys
1               5

<210> SEQ ID NO 16
<211> LENGTH: 17
<212> TYPE: PRT
<213> ORGANISM: artificial sequence
<220> FEATURE:
<223> OTHER INFORMATION: Synthetic peptide

<400> SEQUENCE: 16

Gly Ser Gly Gly Ser Gly Lys Gly Gly Ser Gly Lys Gly Gly Ser Gly
1               5                   10                  15

Lys

<210> SEQ ID NO 17
<211> LENGTH: 10
<212> TYPE: PRT
<213> ORGANISM: artificial sequence
<220> FEATURE:
<223> OTHER INFORMATION: Synthetic peptide

<400> SEQUENCE: 17

Gly Ser Gly Gly Ser Gly Gly Gly Gly Ser
1               5                   10

<210> SEQ ID NO 18
<211> LENGTH: 6
<212> TYPE: PRT
<213> ORGANISM: artificial sequence
<220> FEATURE:
<223> OTHER INFORMATION: Synthetic peptide

<400> SEQUENCE: 18

Gly Gly Ser Gly Gly Lys
1               5

<210> SEQ ID NO 19
<211> LENGTH: 64
<212> TYPE: PRT
<213> ORGANISM: artificial sequence
<220> FEATURE:
<223> OTHER INFORMATION: Synthetic peptide

<400> SEQUENCE: 19

Gly Ser Gly Gly Ser Gly Gly Gly Ser Gly Ser Gly Gly Lys
1               5                   10                  15

Gly Gly Ser Gly Gly Lys Gly Gly Ser Gly Gly Lys Gly Gly Ser Gly
                20                  25                  30

Gly Lys Gly Gly Ser Gly Gly Lys Gly Gly Ser Gly Gly Lys Gly Gly
                35                  40                  45

Ser Gly Gly Lys Gly Gly Ser Gly Gly Lys Gly Gly Ser Gly Gly Lys
                50                  55                  60

<210> SEQ ID NO 20
<211> LENGTH: 127
<212> TYPE: PRT
<213> ORGANISM: Streptomyces avidinii
```

```
<400> SEQUENCE: 20

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 21
<211> LENGTH: 108
<212> TYPE: PRT
<213> ORGANISM: Bradyrhizobium japonicum

<400> SEQUENCE: 21

Gln Gly Leu Pro Ala Pro Ser Tyr Trp Lys Asn Glu Arg Gly Ser Glu
1               5                   10                  15

Leu Leu Ile Trp Ser Ala Asn Ser Gly Thr Ile Gln Gly Thr Phe Thr
            20                  25                  30

Asn His Ala Gln Gly Phe Ala Cys Gln Gly Ile Pro Tyr Pro Ala Ala
        35                  40                  45

Gly Ser Val Ser Pro Thr Gly Leu Tyr Phe Val Val Thr Phe Ala Gln
    50                  55                  60

Cys Asn Ser Phe Thr Arg Trp Val Gly Thr Ile Lys Gly Ser Gln Met
65                  70                  75                  80

Pro Thr Ser Trp Thr Leu Phe Tyr Val Asp Asn Lys Gly Lys Pro Ser
                85                  90                  95

Arg Leu Lys Gly Gly Asp Ile Phe Thr Arg Val Trp
            100                 105

<210> SEQ ID NO 22
<211> LENGTH: 6
<212> TYPE: PRT
<213> ORGANISM: artificial sequence
<220> FEATURE:
<223> OTHER INFORMATION: His tag

<400> SEQUENCE: 22

His His His His His His
1               5
```

MONOMERIC STREPTAVIDIN MUTANTS, METHODS OF USING THE SAME AND PROCESSES OF MANUFACTURING PROTEINS

CROSS-REFERENCE TO RELATED APPLICATIONS

This application claims priority to provisional patent application No. 62/366,241, filed Jul. 25, 2016, the disclosure of which is hereby incorporated by reference.

FIELD OF THE DISCLOSURE

This invention relates generally to the field of streptavidin mutants, as well as processes of manufacturing proteins, including streptavidin mutants. In particular, the invention relates to production and uses of novel, engineered monomeric streptavidin compositions.

BACKGROUND OF THE DISCLOSURE

Streptavidin, which is an avidin homolog from the bacterium *Streptomyces avidinii*, is used broadly in science and engineering because it can bind biotinylated ligands with high affinity. The interaction is robust, context independent and simple to implement. For example, many commonly used protein reagents (e.g. ligands, enzymes and antibodies) are already available in biotinylated forms and can be used readily in (strept)avidin-based detection systems. Streptavidin also has high thermodynamic and chemical stability and can be conjugated with organic molecules or enzymes without loss of function, which is an important attribute for its use in different experiments. Common uses of streptavidin include detection and quantification of biotinylated ligands, as well as immobilization, crosslinking, purification, and labeling of various biotinylated targets. Other uses of streptavidin include fluorescence microscopy or flow cytometric analysis of cells, in which cell surface proteins are enzymatically biotinylated or localized with biotinylated ligands, toxins or antibodies for subsequent labeling with fluorescent streptavidin.

However, labeling of biotinylated targets on live cells with wild type streptavidin (wtSA) can be problematic because of its tetrameric structure, which can result in aggregation of target molecules that interferes with measurements at a molecular level. Target aggregation can be avoided by using monovalent streptavidin, as was shown using an engineered monovalent tetramer containing a single active binding site. Although monovalent tetramer binds biotinylated receptors without target clustering, preparation of the molecule requires in vitro folding and lengthy biochemical separation steps. To simplify monovalent detection of biotinylated targets, an engineered monomeric streptavidin (mSA) has been generated (Lim et al., Biotechnology Bioeng. 110, 57-67, 2013). Despite its useful structural and biochemical properties, currently available mSA, including the one described in Lim et al., have rapid biotin dissociation kinetics ($k_{off}$=1.05×10$^{-3}$ s$^{-1}$ or dissociation $t_{1/2}$=11 min). As such, cells labeled with fluorophore conjugated mSA lose fluorescence over time, resulting in time dependent signal loss that complicates detection and analysis. In this regard, engineering an mSA mutant with a slower dissociation rate is needed to increase its performance in some biotechnology applications, including live cell imaging.

Beyond the above, one of the challenges when using mSA in experiments is the difficulty of its purification. Existing mSA purification protocols are based on inclusion body purification or use a solubilization tag, e.g. maltose binding protein or thioredoxin. Both methods are slow, expensive and require in vitro folding. The difficulty of preparing mSA limits usefulness of the molecule—with or without improvement in the binding characteristics—especially if the end user is unable to prepare the material for a planned study.

There remains a need for a stable, high affinity monomeric streptavidin possessing a slow dissociation rate and which can be easily prepared.

SUMMARY OF THE DISCLOSURE

This disclosure provides stable streptavidin monomers that bind biotin with high affinity and which possess slow dissociation rates, and methods of making and using those monomers. For example, the mutant mSAs have a high denaturation temperature (such as at least 60° C.), and do not unfold and lose function at room temperature (about 20 to 22 C). Also, the protein is highly soluble in aqueous solutions and does not aggregate or precipitate even at high concentration >30 mg/ml. We have solved the limitations of prior streptavidin monomers and engineered monomeric streptavidin with improved denaturation temperature, biotin affinity and performance characteristics for certain biotechnology applications such as live cell imaging. Further, preparation and purification of mSA is simple and yields highly enriched protein compared to existing protocols.

In one aspect, this disclosure provides a mutant streptavidin polypeptide comprising the sequence of SEQ ID NO: 1 in which one or more of the following substitutions are present: i) Serine (S) at position 13 (S13) to arginine (R), or lysine (K); ii) Threonine (T) at position 38 (T38) to phenylalanine (F), tryptophan (W), or tyrosine (Y); iii) Glycine (G) at position 39 (G39) to alanine (A); iv) Glutamic acid (E) at position 104 (E104) to threonine (T), cysteine (C), serine (S), proline (P), aspartic acid (D), glutamine (Q), leucine (L), or valine (V); v) Glutamine (Q) at position 12 (Q12) to Aspartic acid (D) or Glutamic acid (E); or a combination of any of i), ii), iii), iv), v), and v).

In one aspect, the disclosure provides fusion proteins comprising the mutant streptavidin polypeptides provided herein. In one aspect, the disclosure provides mutant streptavidin polypeptides to which additional amino acid sequences have been added at the N- or C-terminus.

In one aspect, the disclosure provides vectors which comprise nucleotide sequences encoding the mutant streptavidin polypeptides provided herein. In one aspect, the disclosure provides host cells comprising the vectors.

In one aspect, this disclosure provides a method of generating and isolating mutant streptavidin polypeptides, which have biotin binding activity. The method comprising introducing vectors into prokaryotic host cells (such as bacteria, such as *E. coli*), growing the bacteria, disrupting the bacteria and allowing the released proteins into the culture medium which contains biotin to form complexes of the recombinant mutant streptavidin with biotin, separating the culture medium from the cells, isolating the released recombinant mutant streptavidin complexed to biotin, and then separating the biotin from the complex to provide isolated monomeric mutant streptavidin polypeptides.

BRIEF DESCRIPTION OF THE FIGURES

FIG. 6. Sequence alignment of wild type streptavidin (wtSA), monomeric streptavidin (mSA), and bradavidin 2 (Brad2) by Clustal Omega is shown in a). The mSA residues mutated in the current study are in bold and boxed in gray. The residue numbers above the sequences are based on customary wtSA residue numbering. Schematic of the expression construct for periplasmic secretion of mSA is shown in b). Key elements of the coding region are indicated. The restriction enzyme recognition sequences are underlined and in italics: SpeI (TS), EcoRI (EF), NheI (AS), BamHI (GS). The entire gene was cloned into pET32 under the control of the T7 promoter using NdeI (5') and XhoI (3') (not shown). The sequence for wtSA is SEQ ID NO:20. The sequence for mSA is SEQ ID NO: 1. The sequence for Brad2 is SEQ ID NO:21. The sequence for OmpA is 12, The sequence for poly His is SEQ ID NO:22, The sequence for FLAG is SEQ ID NO:13. In FIG. 6b, the sequence AEAGIT . . . PSAAS corresponds to the first six and the last five amino acids of mSA, whose complete sequence is provided in SEQ ID NO: 1. FIG. 6b is a composite of SEQ ID NO: 13 (OmpA), SEQ ID NO:22 (6×His), SEQ ID NO:1 (mSA) and SEQ ID NO: 13 (FLAG).

FIG. 9. To evaluate the importance of the biotin additive, mSA was induced without biotin in the medium as shown in a). The culture medium was then pH adjusted to 7.5 and poured over Ni-NTA resin, which immediately turned brown (not shown). 1. Culture medium, 2. Flow through after Ni-NTA, 3. Wash, 4. Elution. The amount of purified mSA was approximately 20% of the expressed protein. See FIG. 3a for comparison. (*) mSA. Thermal denaturation of mSA-RF purified with (circle) and without (square) biotin in the medium is shown in b). Whereas the protein purified with biotin undergoes a clear two state unfolding transition, the unfolding of protein purified without biotin does not show such transition.

DETAILED DESCRIPTION OF THE DISCLOSURE

Figure 1:
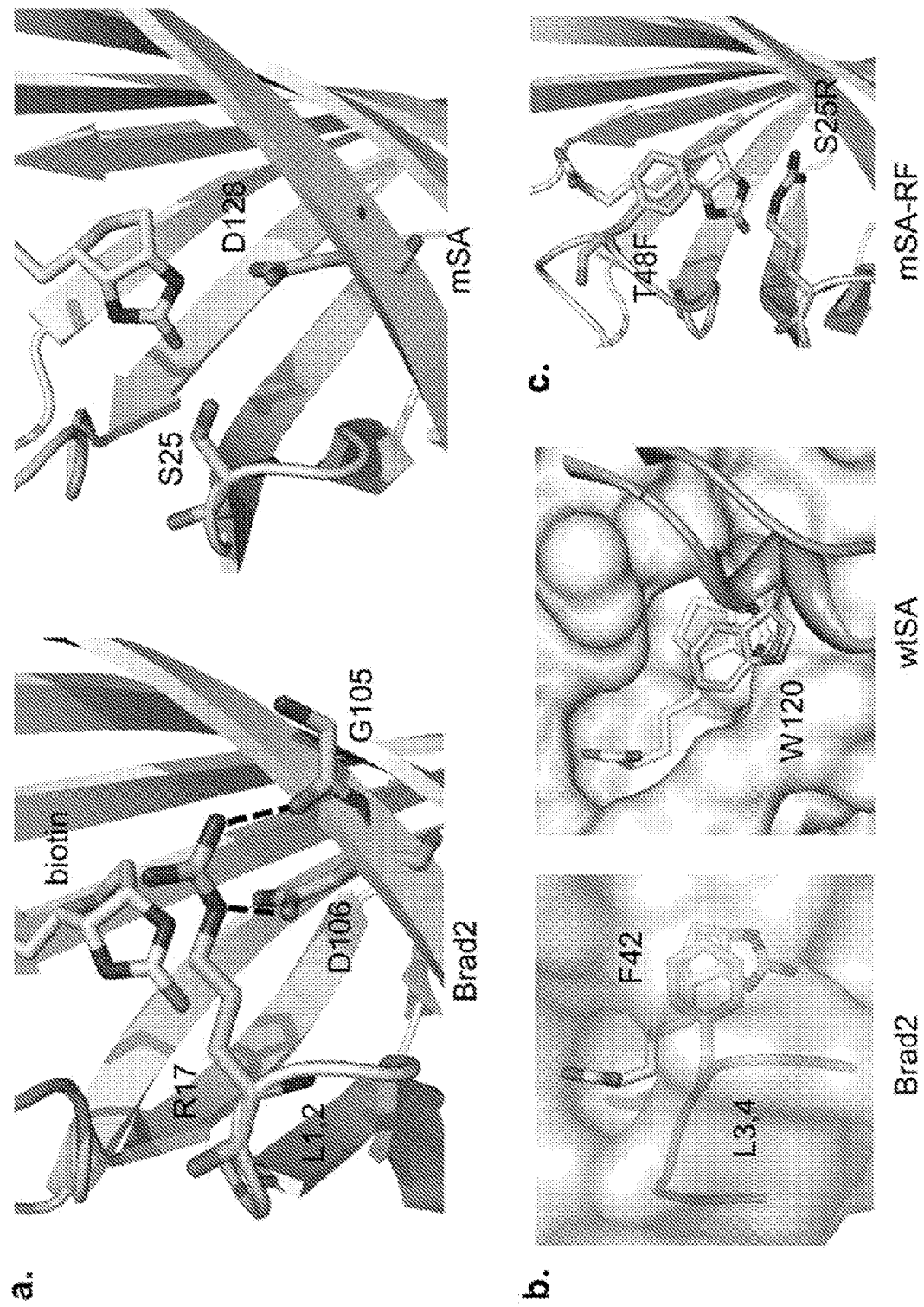
FIG. 1. Rational design of the mSA binding pocket. a) The binding pocket of Brad2 (PDB: 4GGZ) contains R17 that forms a physical barrier around bound biotin through interactions with G105 and D106. Since the corresponding residue in mSA, S25, is small, solvent molecules may enter the binding pocket more easily. b) Brad2 F42 forms a hydrophobic lid that traps biotin in the binding pocket. The residue occupies the same space over bound biotin as W120 of wtSA, which is donated by a neighboring subunit and is that are important for high affinity biotin binding. c) Modeled mSA-RF containing S25R and T48F mutations.

This disclosure provides stable streptavidin monomers that bind biotin with high affinity and which exhibit slow dissociation rates. The disclosure also provides methods of making and using those monomers.

Sequences provided in this disclosure are set forth below. All are amino acid sequences provided in the single letter amino acid code. SEQ ID NO. 1 is mSA (reference sequence). SEQ ID NO: 1-11 are examples of sequences within the scope of the subject invention. SEQ ID NO: 12 is the OmpA signal peptide.

(mSA reference sequence)
SEQ ID NO: 1
AEAGITGTWYNQSGSTFTVTAGADGNLTGQYENRAQGTGCQNSPYTLTGRY
NGTKLEWRVEWNNSTENCHSRTEWRGQYQGGAEARINTQWNLTYEGGSGPA
TEQGQDTFTKVKPSAAS (mSA-R)
SEQ ID NO: 2
AEAGITGTWYNQRGSTFTVTAGADGNLTGQYENRAQGTGCQNSPYTLTGRY
NGTKLEWRVEWNNSTENCHSRTEWRGQYQGGAEARINTQWNLTYEGGSGPA
TEQGQDTFTKVKPSAAS (mSA-RF)
SEQ ID NO: 3
AEAGITGTWYNQRGSTFTVTAGADGNLTGQYENRAQGFGCQNSPYTLTGRY
NGTKLEWRVEWNNSTENCHSRTEWRGQYQGGAEARINTQWNLTYEGGSGPA
TEQGQDTFTKVKPSAAS (mSA-RWT)
SEQ ID NO: 4
AEAGITGTWYNQRGSTFTVTAGADGNLTGQYENRAQGWGCQNSPYTLTGRY
NGTKLEWRVEWNNSTENCHSRTEWRGQYQGGAEARINTQWNLTYEGGSGPA
TTQGQDTFTKVKPSAAS (mSA-H)
SEQ ID NO: 5
AEAGITGTWYNQHGSTFTVTAGADGNLTGQYENRAQGTGCQNSPYTLTGRY
NGTKLEWRVEWNNSTENCHSRTEWRGQYQGGAEARINTQWNLTYEGGSGPA
TEQGQDTFTKVKPSAAS (mSA-ER)
SEQ ID NO: 6
AEAGITGTWYNERGSTFTVTAGADGNLTGQYENRAQGTGCQNSPYTLTGRY
NGTKLEWRVEWNNSTENCHSRTEWRGQYQGGAEARINTQWNLTYEGGSGPA
TEQGQDTFTKVKPSAAS (mSA-DR)
SEQ ID NO: 7
AEAGITGTWYNDRGSTFTVTAGADGNLTGQYENRAQGTGCQNSPYTLTGRY
NGTKLEWRVEWNNSTENCHSRTEWRGQYQGGAEARINTQWNLTYEGGSGPA
TEQGQDTFTKVKPSAAS (mSA-ERF)
SEQ ID NO: 8
AEAGITGTWYNERGSTFTVTAGADGNLTGQYENRAQGFGCQNSPYTLTGRY
NGTKLEWRVEWNNSTENCHSRTEWRGQYQGGAEARINTQWNLTYEGGSGPA
TEQGQDTFTKVKPSAAS (mSA-DRF)
SEQ ID NO: 9
AEAGITGTWYNDRGSTFTVTAGADGNLTGQYENRAQGFGCQNSPYTLTGRY
NGTKLEWRVEWNNSTENCHSRTEWRGQYQGGAEARINTQWNLTYEGGSGPA
TEQGQDTFTKVKPSAAS (mSA-ERWT)
SEQ ID NO: 10
AEAGITGTWYNERGSTFTVTAGADGNLTGQYENRAQGWGCQNSPYTLTGRY
NGTKLEWRVEWNNSTENCHSRTEWRGQYQGGAEARINTQWNLTYEGGSGPA
TTQGQDTFTKVKPSAAS (mSA-DRWT)
SEQ ID NO: 11
AEAGITGTWYNDRGSTFTVTAGADGNLTGQYENRAQGWGCQNSPYTLTGRY
NGTKLEWRVEWNNSTENCHSRTEWRGQYQGGAEARINTQWNLTYEGGSGPA
TTQGQDTFTKVKPSAAS (OmpA signal peptide)
SEQ ID No: 12
MKKTAIAIAVALAGFATVAQA (FLAG epitope)
SEQ ID NO: 13
DYKDDDDK (Combination of modified FLAG and cMyc tags)
SEQ ID NO: 14
GSDAKDRSDKGSEQKLISEEDLGSDAKDSADKGSEQKLISEARKGSDYKD
DDDK (Synthetic peptide)
SEQ ID NO: 15
GGSGK (Synthetic peptide)
SEQ ID NO: 16
GSGGSGKGGSGKGGSGK (Synthetic peptide)
SEQ ID NO: 17
GSGGSGGGS (Synthetic peptide)
SEQ ID NO: 18
GGSGGK (Synthetic peptide)
SEQ ID NO: 19
GSGGSGGGSGGSGGKGGSGGKGGSGGKGGSGGKGGSGGKGGSGGKGGSGG
KGGSGGKGGSGGK (wtSA)
SEQ ID NO: 20
AEAGITGTWYNQLGSTFIVTAGADGALTGTYESAVGNAESRYVLTGRYDSA
PATDGSGTALGWTVAWKNNYRNAHSATTWSGQYVGGAEARINTQWLLTSGT
TEANAWKSTLVGHDTFTKVKPSAAS -continued (Brad2)
SEQ ID NO: 21
QGLPAPSYWKNERGSELLIWSANSGTIQGTFTNHAQGFACQGIPYPAAGSV

SPTGLYFVVTFAQCNSFTRWVGTIKGSQMPTSWTLFYVDNKGKPSRLKGGD

IFTRVW (6 histidine tag)
SEQ ID NO: 22
HHHHHH

As used herein, "AA" refers to "amino acid."

To specify a particular amino acid, the amino acid as identified by its single letter amino acid code, is followed by the position number. For example, S13 in SEQ ID NO:1 would mean the amino acid Serine at position number 13 in the sequence of SEQ ID NO: 1, or the amino acid serine corresponding to the position number 13 in the sequence of SEQ ID NO: 1 (such as in a sequence that is shorter or longer than SEQ ID NO: 1).

Specifically, the present invention provides mutants of monomeric streptavidin. The sequence of monomeric streptavidin is set forth in SEQ ID NO: 1.

In various embodiments, the mutants of the present disclosure comprise a sequence of SEQ ID NO:1 in which one or more of S13, T38, E104, Q12 and G39 are substituted by another amino acid.

In one embodiment of the present invention, the mutant of monomeric streptavidin comprises an AA sequence comprising a mutation wherein S13 (meaning serine at position 13 of SEQ ID NO: 1 or at a position corresponding thereto) is substituted with a positively charged amino acid (arginine (R), histidine (H) or lysine (K)). In a preferred embodiment, S13 is substituted with arginine (R).

In one embodiment of the present invention, the AA sequence of the streptavidin mutant comprises a mutation wherein T38 (meaning threonine at position 38 of SEQ ID NO: 1 or at a position corresponding thereto) is substituted with an AA possessing an aromatic side group, (phenylalanine (F), tryptophan (W), or tyrosine (Y)). In some embodiments wherein the mutant of monomeric streptavidin comprises an AA sequence comprising a mutation wherein S13 is substituted with a positively charged amino acid (R, H or K), the AA sequence further comprises a mutation wherein T38 is substituted with an AA possessing an aromatic side group, (F, W, or Y). In some examples, the AA sequence of the streptavidin mutant comprises mutations wherein S13 is substituted with arginine (R) and T38 is substituted with either phenylalanine (F) or tryptophan (W).

In another embodiment of the present invention, the AA sequence of the streptavidin mutant comprises a mutation wherein E104 (meaning glutamic acid at position 104 of SEQ ID NO: 1 or at a position corresponding thereto) is substituted with an amino acid possessing an uncharged side group (threonine (T), cysteine (C), serine (S), proline (P), aspartic acid (D), glutamine (Q), leucine (L), or valine (V)). In some embodiments wherein the mutant of monomeric streptavidin comprises an AA sequence comprising a mutation wherein S13 is substituted with R, H or K, the AA sequence further comprises a mutation wherein E104 is substituted with an amino acid possessing an uncharged side group (T, C, S, P, D, Q, L, or V). In some embodiments wherein the mutant of monomeric streptavidin comprises an AA sequence comprising a mutation wherein T38 is substituted with an AA possessing an aromatic side group (F, W, or Y), the AA sequence further comprises a mutation wherein E104 is substituted with an amino acid possessing an uncharged side group (T, C, S, P, D, Q, L, or V). In some embodiments wherein the mutant of monomeric streptavidin comprises an AA sequence comprising a mutation wherein S13 is substituted with a positively charged amino acid (R, H or K) and a mutation wherein T38 is substituted with an AA possessing an aromatic side group (F, W, or Y), the AA sequence of the streptavidin mutant of the present invention further comprises a mutation wherein E104 is substituted with an amino acid possessing an uncharged side group (T, C, S, P, D, Q, L, or V). In an example, the AA sequence of the streptavidin mutant of the present invention comprises the following mutations: S13R, T38W and E104T.

In another embodiment of the present invention, the AA sequence of the streptavidin mutant comprises a mutation wherein Q12 (meaning glutamine at position 12 of SEQ ID NO: 1 or at a position corresponding thereto) is substituted with a negatively charged amino acid (aspartic acid (D) or glutamic acid (E)). The substitution results in accelerated biotin dissociation when compared to mutants wherein said substitution is not made. In some embodiments wherein the mutant of monomeric streptavidin comprises an AA sequence comprising a mutation wherein S13 is substituted with a positively charged amino acid (R, H or K), the AA sequence of the streptavidin mutant of the present invention further comprises a mutation wherein Q12 is substituted with a negatively charged amino acid (D or E). In one example, the AA sequence of the streptavidin mutant of the present invention comprises the following mutations: S13R and Q12E. In another example, the AA sequence of the streptavidin mutant of the present invention comprises the following mutations: S13R and Q12D. In added embodiments wherein the mutant of monomeric streptavidin comprises an AA sequence comprising a mutation wherein T38 is substituted with an AA possessing an aromatic side group (F, W, or Y), the AA sequence of the streptavidin mutant further comprises a mutation wherein Q12 is substituted with a negatively charged amino acid (D or E). In some embodiments wherein the mutant of monomeric streptavidin comprises an AA sequence comprising a mutation wherein S13 is substituted with a positively charged amino acid (R, H or K) and a mutation wherein T38 is substituted with an AA possessing an aromatic side group (F, W, or Y), the AA sequence of the streptavidin mutant further comprises a mutation wherein Q12 is substituted with a negatively charged amino acid (D or E). In an example, the AA sequence of the streptavidin mutant of the present invention comprises the following mutations: S13R, T38F and Q12E. In another example, the AA sequence of the streptavidin mutant of the present invention comprises the following mutations: S13R, T38F and Q12D. In some embodiments wherein the mutant of monomeric streptavidin comprises an AA sequence comprising a mutation wherein E104 is substituted with an amino acid possessing an uncharged side group (T, C, S, P, D, Q, L, or V), the AA sequence of the streptavidin mutant further comprises a mutation wherein Q12 is substituted with a negatively charged amino acid (D or E). In some embodiments wherein the mutant of monomeric streptavidin comprises an AA sequence comprising a mutation wherein S13 is substituted with a positively charged amino acid (R, H or K) and a mutation wherein E104 is substituted with an amino acid possessing an uncharged side group (T, C, S, P, D, Q, L, or V), the AA sequence of the streptavidin mutant further comprises a mutation wherein Q12 is substituted with a negatively charged amino acid (D or E). In some embodiments wherein the mutant of monomeric streptavidin comprises an AA sequence comprising a mutation wherein E104 is substituted with an amino acid possessing an uncharged side group (T, C, S, P, D, Q, L, or V) and a mutation wherein T38 is substituted with an AA possessing an aromatic side group (F, W, or Y), the AA sequence of the streptavidin mutant further comprises a mutation wherein Q12 is substituted with a negatively charged amino acid (D or E). In some embodiments wherein the mutant of monomeric streptavidin comprises an AA sequence comprising a mutation wherein S13 is substituted with a positively charged amino acid (R, H or K), a mutation wherein T38 is substituted with an AA possessing an aromatic side group (F, W, or Y) and a mutation wherein E104 is substituted with an amino acid possessing an uncharged side group (T, C, S, P, D, Q, L, or V), the AA sequence of the streptavidin mutant further comprises a mutation wherein Q12 is substituted with a negatively charged amino acid (D or E). In an example, the AA sequence of the streptavidin mutant comprises the following mutations: S13R, T38W, E104T and Q12E. In another example, the AA sequence of the streptavidin mutant of the present invention comprises the following mutations: S13R, T38W, E104T and Q12D.

In one embodiment, the AA sequence of the streptavidin mutant comprises a mutation wherein glycine (G) at position 39 (G39) to alanine (A). In some embodiments wherein the mutant of monomeric streptavidin comprises an AA sequence comprising a mutation wherein S13 is substituted with a positively charged amino acid (R, H or K), the AA sequence of the streptavidin mutant of the present invention also comprises a mutation wherein G39 is substituted with A. In an example wherein the mutant of monomeric streptavidin comprises an AA sequence comprising a mutation wherein T38 is substituted with an AA possessing an aromatic side group (F, W, or Y), the AA sequence of the streptavidin mutant further comprises a mutation wherein G39 is substituted with A. In an example, wherein the mSA mutant comprises a mutation wherein E104 is substituted with an amino acid possessing an uncharged side group (T, C, S, P, D, Q, L, or V), the AA sequence further comprises a mutation where G39 is substituted with A. In an example, wherein the mSA mutant comprises a mutation wherein Q12 is substituted with a negatively charged amino acid (D or E), the AA sequence further comprises a mutation wherein G39 is substituted with A. In an example, wherein the mSA mutant comprises a mutation wherein S13 is substituted with a positively charged amino acid (R, H or K) and T38 is substituted with an AA possessing an aromatic side group (F, W, or Y), the AA sequence further comprises a mutation wherein G39 is substituted with A. In an example, wherein the mSA mutant comprises a mutation wherein S13 is substituted with a positively charged amino acid (R, H or K) and E104 is substituted with an amino acid possessing an uncharged side group (T, C, S, P, D, Q, L, or V), the AA sequence further comprises a mutation wherein G39 is substituted with A. In an example, wherein the mSA mutant comprises a mutation wherein S13 is substituted with a positively charged amino acid (R, H or K) and Q12 is substituted with a negatively charged amino acid (D or E), the AA sequence further comprises a mutation wherein G39 is substituted with A. In an example wherein the mSA mutant comprises a mutation wherein T38 is substituted with an AA possessing an aromatic side group (F, W, or Y), E104 is substituted with an amino acid possessing an uncharged side group (T, C, S, P, D, Q, L, or V), the AA sequence further comprises a mutation wherein G39 is substituted with A. In an example wherein the mSA mutant comprises a mutation wherein T38 is substituted with an AA possessing an aromatic side group (F, W, or Y), Q12 is substituted with a negatively charged amino acid (D or E), the AA sequence further comprises a mutation wherein G39 is substituted with A. In an example wherein the mSA mutant comprises a mutation wherein E104 is substituted with an amino acid possessing an uncharged side group (T, C, S, P, D, Q, L, or V), Q12 is substituted with a negatively charged amino acid (D or E), the AA sequence further comprises a mutation wherein G39 is substituted with A. In an example wherein the mSA mutant comprises a mutation wherein S13 is substituted with a positively charged amino acid (R, H or K) and T38 is substituted with an AA possessing an aromatic side group (F, W, or Y), E104 is substituted with an amino acid possessing an uncharged side group (T, C, S, P, D, Q, L, or V), the AA sequence further comprises a mutation wherein G39 is substituted with A. In an example wherein the mSA mutant comprises a mutation wherein S13 is substituted with a positively charged amino acid (R, H or K) and T38 is substituted with an AA possessing an aromatic side group (F, W, or Y), Q12 is substituted with a negatively charged amino acid (D or E), the AA sequence further comprises a mutation wherein G39 is substituted with A. In an example wherein the mSA mutant comprises a mutation wherein S13 is substituted with a positively charged amino acid (R, H or K) and E104 is substituted with an amino acid possessing an uncharged side group (T, C, S, P, D, Q, L, or V), Q12 is substituted with a negatively charged amino acid (D or E), the AA sequence further comprises a mutation wherein G39 is substituted with A. In an example wherein the mSA mutant comprises a mutation wherein T38 is substituted with an AA possessing an aromatic side group (F, W, or Y), E104 is substituted with an amino acid possessing an uncharged side group (T, C, S, P, D, Q, L, or V), and Q12 is substituted with a negatively charged amino acid (D or E), the AA sequence further comprises a mutation wherein G39 is substituted with A. In an example wherein the mSA mutant comprises a mutation wherein S13 is substituted with a positively charged amino acid (R, H or K), T38 is substituted with an AA possessing an aromatic side group (F, W, or Y), E104 is substituted with an amino acid possessing an uncharged side group (T, C, S, P, D, Q, L, or V), and Q12 is substituted with a negatively charged amino acid (D or E), the AA sequence further comprises a mutation wherein G39 is substituted with A.

In preferred embodiments, the streptavidin mutant comprises an AA sequence comprising mutations wherein S13 is substituted with arginine (R) and T38 is substituted with either phenylalanine (F) or tryptophan (W).

The monomeric streptavidin of the present invention may be followed at the c-terminus by a peptide (i.e., fused at the C-terminus, i.e. mSA-peptide). The peptide may be a disordered peptide sequence containing one or more K's for amine conjugation with fluorophores or enzymes. The peptide can be of any length. Exemplary peptides include:

```
FLAG epitope
(DYKDDDDK-SEQ ID NO: 13), a combination of modified FLAG and cMyc tags
(GSDAKDRSDKGSEQKLISEEDLGSDAKDSADKGSEQKLISEARKGSDY

KDDDDK-SEQ ID NO: 14), repeats of GGSGK (SEQ ID NO: 15)

(e.g., GSGGSGKGGSGKGGSGK-SEQ ID NO: 16),
and
```

-continued a GSGGSGGGGS (SEQ ID NO: 17) linker followed by
9 repeats of

GGSGGK (SEQ ID NO: 18)

(GSGGSGGGGSGGSGGKGGSGGKGGSGGKGGSGGKGGSGGKGGSGGKGG

SGGKGGSGGKGGSGGK-SEQ ID NO: 19).

In one embodiment, the peptide may contain repeats of original or modified FLAG or cMyc epitope tags followed by a translational stop. In another embodiment, the peptide may contain >5 repeats of GGSGGK (SEQ ID NO:18) followed by a translational stop.

In some embodiments, complex of biotin with the streptavidin mutants of the present invention possess half-lives ($t_{1/2}$) of greater than 30, 40, 50, 60, 70, 80, 90, 100, 150, 200, 250, 300, 350, or 400 minutes. In preferred embodiments, the biotin-streptavidin mutants possess half-lives ($t_{1/2}$) of greater than 150, 200, 250, 300, 350 or 400 minutes. In some examples, the biotin-streptavidin mutants possess half-lives ($t_{1/2}$) of greater than 250 minutes.

The biotin dissociation rate ($k_{off}$) for the biotin-mSA mutants can range from $1.7 \times 10^{-3}$ min$^{-1}$ to $63 \times 10^{-3}$ min$^{-1}$. In one embodiment, the $k_{off}$ can be from $1 \times 10^{-3}$ min$^{-1}$ to $60 \times 10^{-3}$ min$^{-1}$. In various embodiments, the $k_{off}$ can be from $1.5 \times 10^{-3}$ min$^{-1}$ to $60 \times 10^{-3}$ min$^{-1}$, from $1.5 \times 10^{-3}$ min$^{-1}$ to $50 \times 10^{-3}$ min$^-1$, from $1.5 \times 10^{-3}$ min$^{-1}$ to $30 \times 10^{-3}$ min$^{-1}$, from $1.5 \times 10^{-3}$ min$^{-1}$ to $20 \times 10^{-3}$ min$^-1$, from $2 \times 10^{-3}$ min$^{-1}$ to $20 \times 10^{-3}$ min$^{-1}$ and all values between these ranges. The $K_d$ of the biotin-mutant mSA complexes can be measured. Examples of $K_d$ for mSA-RF and mSA-RWT mutants (see Table 1) include about 1 to 10 nM.

The invention also provides mutant streptavidin polypeptide present in a fusion protein or conjugate, wherein the fusion protein comprises a mSA mutant and at least another protein or peptide. The other protein or peptide may be at the N- or C-terminus or both of the mSA. In one embodiment, the fusion protein comprises a mutant streptavidin as disclosed herein fused to any desired amino acid sequence. In one embodiment, the fusion protein is a protein of interest (POI) for in vivo proximity biotinylation. In another embodiment, the fusion protein is a genetic fusion to introduce a biotin binding tag. For example, mSA can be fused to a cell penetrating peptide to create a novel cell transduction module capable of mediating cellular import of arbitrary biotinylated cargo. In a further embodiment, the mutant streptavidin may be fused or conjugated with a reporter molecule, such as an enzyme or a fluorophore. In another embodiment, the mutant streptavidin may be fused or conjugated with a nucleic acid. While the sequence of the proteins provided herein can be synthesized using any suitable method, it is preferable to make it by using an inventive process as provided herein. The advantage of using the present method is that the protein is obtained as properly folded and the yield is significant.

The invention further provides complexes comprising a mutant streptavidin protein, which may include a fusion protein or conjugate, and a biotinylated molecule. Biotinylated molecules include, but are not limited to, biotinylated nucleic acids, carbohydrates, lipids, antibodies, peptides and polypeptides. In one embodiment, the biotinylated molecule may be a biotinylated antibody, and the mutant streptavidin may be fused or conjugated with a reporter molecule, such as an enzyme or a fluorophore. In another embodiment, the biotinylated molecule may be a biotinylated antibody, and the mutant streptavidin may be fused or conjugated with a nucleic acid. In a further embodiment, the biotinylated molecule and the conjugated mutant streptavidin may be pre-mixed to form a non-covalent complex conjugated with a reporter. In a further embodiment, the biotinylated molecule and the fused mutant streptavidin may be pre-mixed to form a non-covalent complex fused with a reporter. Biotinylated molecules are also considered to include molecules conjugated to biotin analogues and biotin derivatives such as iminobiotin and desthiobiotin.

The invention additionally provides compositions comprising polynucleotide sequences encoding each and every monomeric streptavidin protein described herein, including all combinations of the various mutations described herein. The polynucleotide sequence may be present in an expression vector or other types of vectors, such as shuttle vectors, and may be used to express the proteins in any suitable cell type, including but not necessarily limited to bacterial, yeast, insect and mammalian cells. The polynucleotides may be provided in a composition comprising a cell culture. The polynucleotides may also be provided in a kit with other reagents useful for expressing and/or purifying the proteins from the cell culture or for using the proteins encoded by the polynucleotides in any of a variety of assays and/or other processes. The polynucleotides may be linked to one or more cloning sites, such as a polycloning site, which would facilitate synthesis of fusion proteins comprising a protein of the invention fused to any desired amino acid sequence. The present invention also provides a kit comprising i) said polynucleotides and optionally, said reagents; and ii) instructions for use according to the methods of the subject invention.

The invention additionally provides a protein purification system that enables production and selective purification of a protein that is encoded in the same reading frame as a protein of the invention. For example, the fusion proteins can be isolated and/or purified to any desired degree of purity using a biotin resin/column (e.g. 6×His tag for purification on nickel or cobalt resin).

The monomeric streptavidin proteins of the present invention can be used to label/immobilize biotinylated compounds without causing aggregation of the targeted molecule. Aggregation of the targeted molecules is a concern if wild type streptavidin is used as a labeling reagent. For example, adding wild type (wt) tetrameric streptavidin to cells expressing biotinylated cell surface proteins induces the proteins to aggregate because the lipid bilayer is fluid and allows the proteins to laterally diffuse. A solution to this problem involves monovalent streptavidin, in which three binding sites have been mutated to prevent biotin binding. Preparing the reagent, however, is difficult because it is a multi-step process involving recombinant expression, denaturation, renaturation and purification, thus significantly adding to the total labor. Thus, the monomeric streptavidin proteins described herein provide improved composition for labeling and/or immobilizing biotinylated compounds.

Monomeric streptavidin (mSA) selectively binds biotinylated ligands on the cell surface and produces diffusely labeled images by total internal reflection fluorescence spectroscopy. In contrast, wtSA labeling of the same cells produces punctuated structures, indicative of target clustering caused by multivalent interaction since such aggregated target molecules may be internalized and thereby concentrated in vesicles. mSA can also be used in superresolution microscopy to obtain static and dynamic information on the distribution and movement of biotinylated proteins on cultured neurons. In particular, fluorophore conjugated mSA is able to specifically interact with biotinylated ligands on the cell surface without perturbing their natural distribution or movement. Using single molecule tracking, labeling with wtSA perturbs the distribution and dynamics of labeled molecules at a molecular level. Because mSA is small (MW 13 kDa), it can enter crowded spaces, such as the neural synapse, more easily than wtSA (53 kDa) or antibody (150 kDa), which may be useful when studying some biological systems. Because monomeric streptavidin is a structural monomer, it can also be used as a genetic fusion to introduce a biotin binding tag. For example, mSA can be fused to a cell penetrating peptide to create a novel cell transduction module capable of mediating cellular import of arbitrary biotinylated cargoes. mSA can also be fused to a protein of interest (POI) for in vivo proximity biotinylation. In this context, mSA can be used to recruit a reactive biotin species to the fusion protein and selectively biotinylate neighboring proteins in a distance dependent manner. Subsequent disruption of the mSA-biotin interaction and affinity purification of biotinylated molecules on streptavidin resin can then be used to identify the proteins that potentially interact with the POI. All of the foregoing inventive methods are initiated by allowing the mSA or mSA fusion construct to contact the biotin or the biotinylated molecule. When the method is performed in vivo, said contact may occur via administration to a subject.

The present invention also provides a method of isolating a biotinylated molecule comprising providing a composition comprising biotinylated molecules, contacting the biotinylated molecules with a mutant streptavidin protein of the present invention, allowing formation of mutant streptavidin-biotinylated molecule complexes, and separating the complexes from other components of the composition. Biotinylated molecules are also considered to include molecules conjugated to biotin analogues and biotin derivatives such as iminobiotin and desthiobiotin.

In one embodiment, the invention provides a method for isolating a biotinylated molecule, examples of which include, but are not limited to, biotinylated nucleic acids, carbohydrates, lipids, antibodies, peptides and polypeptides. Biotinylated molecules are also considered to include molecules conjugated to biotin analogues and biotin derivatives such as iminobiotin and desthiobiotin. The method comprises providing a composition comprising biotinylated molecules, contacting the biotinylated molecules with at least one mutant streptavidin protein provided by the invention, allowing formation of mutant streptavidin-biotinylated molecule complexes, and separating the complexes from other components of the composition. By mutant streptavidin-biotinylated molecule "complex" it is meant that the mutant streptavidin is bound to the biotin moiety of the biotinylated molecule. Either the mutant streptavidin protein or the biotinylated molecules can be attached to a substrate, such as a resin, beads, a column, etc. If the biotinylated molecules are attached to a substrate, the method can function to isolate the mutant streptavidin molecules from a composition, which has particular value, for example, when screening fusion proteins comprising a mutant streptavidin protein of the invention wherein the non-mutant streptavidin portion of the fusion protein comprises the amino acid sequence of a protein of interest.

The subject invention further provides a kit comprising i) a mutant streptavidin protein of the subject invention, a fusion protein or conjugate thereof, or a complex comprising a mutant streptavidin protein of the subject invention and a biotinylated molecule and ii) instructions for use according to the methods of the subject invention. In an embodiment, the kit may further comprise biotin or a biotinylated molecule. Biotinylated molecules include, but are not limited to, biotinylated nucleic acids, carbohydrates, lipids, antibodies, peptides and polypeptides. Biotinylated molecules are also considered to include molecules conjugated to biotin analogues and biotin derivatives such as iminobiotin and desthiobiotin. In one embodiment, the biotinylated molecule may be a biotinylated antibody, and the mutant streptavidin may be fused or conjugated with a reporter molecule, such as an enzyme or a fluorophore. In another embodiment, the biotinylated molecule may be a biotinylated antibody, and the mutant streptavidin may be fused or conjugated with a nucleic acid. In a further embodiment, the biotinylated molecule and the conjugated mutant streptavidin may be pre-mixed to form a non-covalent complex conjugated with a reporter. In a further embodiment, the biotinylated molecule and the fused mutant streptavidin may be pre-mixed to form a non-covalent complex fused with a reporter.

This disclosure also provides a method of synthesis and purification of monomeric streptavidin mutants. The method is based on the unexpected observation that the recombinant mSA is secreted into the culture medium. As such, the culture medium can be separate from the bacterial cells and then the mSA mutants can be purified from the culture medium. An unexpectedly high yield was obtained by inclusion of biotin in the culture medium. For example, biotin is included in the culture medium at a concentration of from 10 $\mu$M to 1.0 mM and all values and ranges therebetween. In various embodiments, the biotin concentration in the medium can be 50 $\mu$M to 900 $\mu$M, from 100 to 900 $\mu$M, from 200 to 900 $\mu$M, from 300 to 900 $\mu$M, from 400 to 900 $\mu$M, from 500 to 900 $\mu$M, from 600 to 900 $\mu$M, from 700 to 900 $\mu$M. In various embodiments the concentration of biotin in the medium may be 10, 50, 100, 150, 200, 250, 300, 350, 400, 450, 500, 550, 600, 650, 700, 750, 800, 850, 900, 950, and 1000 $\mu$M. It is considered that the presence of biotin in the culture medium allows it to fold and form disulfide bonds. Once the disulfide bonds are formed, the complex can be exposed to denaturing conditions to release biotin, but the mSA does not precipitate out and continues to exist in a folded configuration. If there is no biotin in the medium, the amount of mSA recovered is not very high, and more importantly, does not show meaningful activity for binding to biotin. Thus, to recover active mSA, biotin is needed in the culture medium.

The mutants described in this disclosure, including the secreted recombinant proteins can be produced through the application of recombinant DNA technology. Producing the proteins recombinantly generally comprises initially introducing an expression vector encoding the protein into any suitable host cells by any method known in the art. Methods vary depending upon the type of cellular host, and include but are not limited to transfection employing cationic liposomes, electroporation, calcium chloride, rubidium chloride, calcium phosphate, DEAE-dextran, microinjection, or other substances. These methods are known in the art. In certain embodiments the cells used to produce the protein recombinantly are prokaryotes, including but not necessarily limited to E. coli. (See generally, Sambrook et al., Molecular Cloning, 2nd ed., Cold Spring Harbor Laboratory, Cold Spring Harbor Laboratory Press, Cold Spring Harbor, N.Y., 1989) or other similar lab manuals. Host cells carrying the expression vector can be identified through the use of the selectable marker, and the presence of the gene of interest can be confirmed by hybridization, PCR, antibodies, or other techniques.

Recombinant constructs encoding a protein of interest typically include an expression control sequence operably-linked to the coding sequence of the protein of interest. A "recombinant mSA" (which may be referred to simply as mSA) includes all of the mutants described herein. A reference to a nucleotide sequence "encoding" or "coding for" a protein means that the nucleotide sequence can be translated to the amino acid sequence of the protein. The nucleotide sequence may or may not contain an actual translation start codon or termination codon.

For expression of the recombinant mSA, the nucleic acid containing the nucleotide sequence encoding a mutant mSA can be inserted into an appropriate cloning vector, or an expression vector (i.e., a vector that contains the necessary elements for the transcription and translation of the inserted polypeptide coding sequence) by recombinant DNA techniques well known in the art. Expression vectors useful in recombinant DNA techniques may be in the form of plasmids. The terms "plasmid" and "vector" may be used interchangeably.

In one embodiment, the recombinant expression vectors comprises a nucleic acid encoding an mSA mutant and are present in a host cell. The recombinant expression vectors also comprises one or more regulatory sequences, generally selected on the basis of the host cells to be used for expression that is operatively-linked to the nucleic acid sequence to be expressed. Within a recombinant expression vector, the term "operably-linked" means that the nucleotide sequence of interest is linked to the regulatory sequence(s) in a manner that allows for expression of the nucleotide sequence. A regulatory sequence includes promoters, enhancers and other expression control elements. Such regulatory sequences are well known in the art. Regulatory sequences include those that direct constitutive expression promoters as well as inducible promoters—i.e., those that direct expression of the nucleotide sequence only under certain conditions.

Expression of the mutant mSA polypeptides in prokaryotes is most often carried out in *E. coli* with vectors directing the expression of either fusion or non-fusion polypeptides. Any protein provided by this disclosure can be modified. For example, a protein may be engineered to include a leader or secretory sequence or a sequence which can be used for purification e.g., a His-tag, and/or to include a proteolytic cleavage site. Modifications can be made at the N-terminus, C-terminus. Such modifications can be made using known reagents and techniques, given the benefit of the present disclosure. In embodiments, the protein is modified so that it has, for example, additional or fewer amino acids than in a naturally occurring counterpart.

In one embodiment, fusion vectors may direct the polypeptide to the periplasmic space or direct the secretion of the polypeptide from the cell. A proteolytic cleavage site may be introduced at the junction of the fusion moiety and the recombinant polypeptide to facilitate separation of the recombinant polypeptide from the fusion moiety subsequent to purification of the fusion polypeptide.

In some embodiments, a signal peptide may be used to export proteins to the periplasm between the inner and outer membranes. By placing a signal sequence in front of the coding sequence of the desired protein, the expressed protein can be directed to a particular export pathway. Known export pathways in *E. coli* include the SecB-dependent (SEC), the twin-arginine translocation (TAT), and the signal recognition particle (SRP) pathway. Translocation in the SEC or TAT pathway is via a post-translational mechanism, whereas the SRP pathway translocation is co-translational. Proteins translocated by the SEC pathway are unfolded prior to export and then refolded in the periplasm. In the TAT pathway, the proteins are translocated in a folded state. Examples of other signal sequences that can be used to secrete proteins in *E. coli* include, but are not limited to, Pectate lyase B (PelB) from *Erwinia carotovora*; Outer-membrane protein A (OmpA); Heat-stable enterotoxin 2 (StlI); Endoxylanase (Endo) from *Bacillus* sp.; Alkaline phosphatase (PhoA); Outer-membrane pore protein F (OmpF); Outer-membrane pore protein E (PhoE); Maltose-binding protein (MalE); Outer-membrane protein C (OmpC); Murein lipoprotein (Lpp); Lamba receptor protein (LamB); Protease VII (OmpT); and Heat-labile enterotoxin subunit B (LTB).

In one aspect, this disclosure provides host cells into which a recombinant expression vector has been introduced. The host cells comprising the recombinant expression vector include the progeny of the cells into which the recombinant expression vector has been introduced.

A mutant host cell that includes an expression vector, such as a prokaryotic host cell in culture, can be used to produce (i.e., express) the recombinant mSAs. In one embodiment, the method comprises culturing the host cell of invention (into which a recombinant expression vector encoding the mSA has been introduced) in a suitable medium such that the protein of interest is produced. In another embodiment, the method further comprises the step of isolating the protein of interest from the medium or the host cell. Once expressed, the mutant mSA can be purified from culture media and/or host cells. The mSA can be purified according to standard procedures of the art, including high performance liquid chromatography (HPLC) purification, column chromatography, gel electrophoresis and the like. In one embodiment, the culture medium contains biotin, which forms a complex with the mSA thereby facilitating its proper folding and retention of activity. The recombinant mSA can contain a poly His tag for easy isolation from the culture medium by using Ni columns.

The invention also provides a method for synthesis and purification of monomeric streptavidin compositions wherein the OmpA signal peptide (SEQ ID No: 12) is fused to a monomeric streptavidin. In an example, an expression vector may comprise a monomeric streptavidin sequence downstream of a sequence coding for the outer membrane protein A (OmpA) signal peptide (SEQ ID No: 12), which is followed by the SpeI restriction enzyme recognition sequence and a 6×His tag, which is in turn followed by two restriction sites for EcoRI and NheI (as shown in FIG. 6b). The monomeric streptavidin is cloned using NheI and BamHI and is followed by the FLAG epitope tag (DYKDDDDK (SEQ ID NO: 13)—Stop) and a XhoI site (also shown in FIG. 6b).

For the isolation of mSA mutants that are secreted into the culture medium, it is preferred to use a culture medium containing biotin. To prepare culture medium containing biotin, the microbial growth medium and biotin (as raw powder) can be mixed and dispersed or dissolved in water (separately or together), autoclaved, cooled (such as to 20° C.) and then used as a culture medium. The microbial growth medium generally comprises glycerol, peptides, amino acids, vitamins and carbohydrates. An exemplary microbial growth medium is Terrific Broth, which comprises yeast extract, tryptone, $K_2HPO_4$ and $KH_2PO_4$ (available commercially, e.g., from Sigma-Aldrich).

Once the cells have expanded in culture to desired levels (the density can be measured by measuring the optical density of the culture), the cells and/or the culture medium can be used for isolation of the mSA proteins. In this disclosure, it was unexpectedly observed that significant amounts of mSA proteins are secreted into the medium, and thus could be recovered from the medium instead of isolating them from the *E. coli*. After the culture has reached a desired density, the medium can be separated from the cells by centrifugation.

In one embodiment, prior to recovery of the mSA from the culture medium and prior to separation of the cells, vigorous shaking is carried out which facilitates in the release of the mSA proteins into the culture medium. The shaking results in increasing the viscosity of the culture medium, likely due to lysis of the bacteria. Sonication can be performed, either before or after separation of the cells/cellular material. Sonication can be performed until the viscosity is lowered to values close to the original viscosity of the culture medium. Sonication can be performed by routine methods. For example, sonication can be performed by a 200 W sonicator at about 50% amplitude capacity for about 4 cycles, wherein each cycle consists of about 30 seconds of sonication and about 30 seconds of rest.

The sonicated materials can then be applied to isolation and/or purification steps. The materials can be centrifuged or filtered to remove any cellular materials including debris. Removal of the cellular materials and debris results in clarification of the culture medium. The medium may then be passed over a Ni column to isolate poly His tagged recombinant mSAs. Non-specific binding of non-tagged proteins may be reduced by the use of imidazole. For example, in one embodiment, 10 mM imidazole may be added to the medium. In one embodiment, the purification step (s) comprises: (i) adjusting the pH of the sonicated mixture to about 7.5; ii) adding imidazole to the pH-adjusted mixture of step (i) to form a mixture; iii) centrifuging the mixture of step (ii); iv) passing the centrifuged mixture of step (iii) through a chromatography column; v) washing the chromatography column; vi) eluting bound protein from the chromatography column; vii) concentrating the eluted protein; and viii) removing bound biotin to obtain purified protein. An example of purification is provided in Example 1.

Following isolation of the biotin-mSA complex on the column, the complex can be eluted by using a high concentration of imidazole (such as 300 mM imidazole in PBS). The eluted protein may be concentrated, such as by using centrifugal filters (e.g., Amicon) such as having a cutoff at 10 kDa.

Various methods may be used to release biotin. For example, biotin may be released from the mSA. For example, conditions such as low pH (such as about 2), high temperature (such as higher than 60° C., such as 60-75° C.), buffer exchange (such as with PBS), or a combination of one or more of these conditions may be used. To achieve low pH, any suitable buffer may be used. For example, a glycine buffer (generally at a pH of 1 to 3), or acidic acetate and the like may be used. In one embodiment, the bound biotin is removed by buffer exchange. The buffer exchange can be performed to 100 mM glycine buffer at a pH of about 2.3. The glycine buffer can then be further exchanged to PBS.

In contrast to the affinity of wt streptavidin for biotin, the mSA has lower binding affinity for biotin. This allows easier separation of biotin that is bound to mSA. It was unexpectedly observed that once binding to biotin allows mSA to form disulfide bonds (and therefore fold correctly)—such as by inclusion of biotin in the culture medium, the subsequent exposure (and likely denaturation) of the proteins to conditions required to release biotin does not prevent the mSA from folding back in a proper orientation to again have binding activity.

The activity of isolated mSA can be evaluated by determining binding to biotin. For example, biotinylated compounds may be immobilized on a column or resin and the recovered mSA may be passed through it, and binding to biotin may be evaluated. In one embodiment, gel shift assays may be used where the recovered mSA is mixed with a biotinylated protein (such as a singly biotinylated protein), and run on a native gel (without SDS). A control gel sample may be run with only mSA. If a shift in migration is seen where the mSA was allowed to complex with biotin prior to the run, then that is an indication of biotin binding activity of the mSA.

The amount of mSA recovered when no biotin was used in the culture medium was observed to be about 20% of the amount recovered when biotin was included in the culture medium. The amount recovered when biotin was used can be at least 100 mg/L of the culture medium. In one embodiment, it can be at least 500 mg/L of the culture medium. In one embodiment, it can be from about 100 mg/L to about 500 mg/L of the culture medium. The present method of generating functionally active mSA mutants can be scaled up without deviating from the teachings herein so that larger amounts of the mutants can be made in a bioreactor. The recovered mSA (when biotin was included in the culture medium) was found to be active, as evidenced by its binding to biotin (as measured by gel shift assays or binding to biotin/biotinylated proteins immobilized on resins), or from circular dichroism data.

Those skilled in the art will recognize that routine modifications to these embodiments can be made to the embodiments described herein. For example, the invention includes streptavidin monomers of various lengths, and with various amino acid substitutions, based on the amino acid sequences of the monomers provided by the invention. For example, any peptide described herein can be modified by conservative amino acid substitutions that are based generally on relative similarity of R-group substituents. Non-limiting examples of such substitutions contemplated in the present invention include, but are not limited to: gly or ser for ala; lys, his, asp, or glu for arg; gln or his for asn; glu or asn for asp; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, streptavidin monomers that comprise any single conservative amino acid substitution, or any combination of conservative amino acid substitutions, are included in the invention, so long as they retain their stability, folding and biotin binding properties. Loops residues that do not contact bound biotin may also be deleted or added while preserving the function of streptavidin monomers. In some embodiments, the streptavidin monomers provided by the invention can comprise one, two, three, four, or five conservative amino acid substitutions.

Each streptavidin monomer described herein can also be truncated by any number of amino acids at its N-terminus or C-terminus, and by any number of amino acids at both the N- and C-termini, so long as the remaining sequence retains its stability, folding and biotin binding activities, $K_{off}$ and other properties described herein. Each of the foregoing fragments can also be subjected to the aforementioned amino acid substitutions, and thus, fragments having such substitutions are included within the scope of the invention. Any of the streptavidin monomers provided by the invention can be at least 110 amino acids in length. Each streptavidin monomer described herein can also be extended by any number of amino acids at either N-terminus or C-terminus, at both the N- and C-termini, so long as the final sequence retains its stability and biotin binding activities.

Monomeric streptavidin is simpler to work with than a dimer or a tetramer for both biochemical and genetic manipulations. For example, it can be recombinantly fused, using techniques known in the art, to another protein to construct a bi-functional molecule. In contrast, the use of oligomeric streptavidin as a fusion protein is limited to only a small number of applications. Monomeric streptavidin fused to a protein of interest was used in proximity dependent biotinylation to identify interacting proteins. mSA fused to the Z domain of protein A can recognize an antibody-antigen complex and induce proximity dependent biotinylation of interacting proteins. Another example of recombinant mSA fusion includes a cellular transduction module containing a cell penetrating peptide to bind a biotinylated target and import the target molecule into cells. The engineered mSA encourages a modular approach because the protein can be genetically encoded and subsequently used for specific recognition of biotinylated targets. The affinity of all mSA engineered to date, including the mutants described here, is substantially lower than that of wtSA ($K_d$~10 fM).

Fluorescent microscopy can be used to measure the distribution and dynamics of molecules on the cell surface. Monovalent detection is needed for these applications, because clustering affects the natural state of the target molecule and biases the measurement. Because fluorophore conjugated mSA binds biotinylated targets without aggregating them, it can be used for imaging molecular events on live cells. For example, mSA fused to different fluorescent dyes can be used to image a variety of proteins at the neuronal synapse, including neuroligin, neurexin 1β, leucine-rich repeat transmembrane protein 2, and stargazin, using superresolution microscopy techniques, stochastic optical reconstruction microscopy (STORM), stimulated emission depletion (STED), and universal point accumulation for imaging in nanoscale topography (uPAINT) (Chamma et al., 2016, *Nat Commun*, 7, 10773). Fluorophore conjugated mSA interacts specifically with target molecules even though the conjugated dyes are hydrophobic and prone to non-specific interactions with the membrane. The small size of mSA allowed easier access to the crowded synaptic space compared to streptavidin or antibody, which were slow to enter the synaptic space. Since organic dyes are often brighter than fluorescent proteins and are available with a wide range of convenient excitation and emission wavelengths, mSA conjugated with these fluorophores can be used to prepare live samples for various imaging studies. The slowly dissociating mSA mutants described here facilitate labeling applications in which premature biotin dissociation interferes with data collection.

The existing mSA purification methods are based on cytoplasmic expression and include in vitro folding and proteolytic removal of the solubilization tag. The revised purification protocol based on periplasmic secretion, as described here, represents an important progress because it simplifies bacterial purification of mSA and improves accessibility of the molecule. Whereas the OmpA signal sequence only targeted the expressed protein to the periplasm, we found that mSA was unexpectedly released to the medium. The mechanism by which mSA is released from the periplasm to the medium is not clear but mechanical stress may play a role by disrupting outer membrane, which then allows mSA to leak out during induction. Shaking may also lyse some cells and release enzymes, e.g. lysozymes, that in turn degrade the cell wall and help release mSA from the periplasm. Proteins in the periplasm are known to be exported to the medium by a variety of mechanisms, including the autotransporters, chaperone/usher and type II pathways. As such, mSA yield may be further improved through co-expression of helper proteins, cell permeabilization through enzymatic, chemical and mechanical means, or use of leaky mutant strains.

The streptavidin mutants of the present disclosure can be used for various biotin binding applications. For example, the mutants can be used in a column or as a resin for isolation of biotinylated peptides or proteins. While the affinity of the mutants for biotin is strong enough to isolate biotinylated proteins, the bound biotin can be dissociated from the mutant streptavidin by a variety of methods as described herein (e.g., low pH, high temperature, buffer exchange etc.). Because such methods do not denature the mutant streptavidin, it can be reused.

Throughout this application, various theories may be advanced. These theories are not intended to be binding on the invention in any way. The following example is provided to further illustrate the invention. The specifics of the example are not intended to be limiting in any way.

Example 1

This example describes the construction of a vector comprising a sequence encoding mSA mutants, and a sequence encoding OMPA, and the introduction of the vector into prokaryotic cells (*E. coli*). The example also describes production and isolation of mSA proteins produced by the culture of the recombinant cells.

Residues described in this example utilize mSA (SEQ ID No: 1) as the reference sequence to which mutations are made but with use of residue numbers from wild type streptavidin (wtSA) as shown in FIG. 6. Residue 24 in this example corresponds to residue 12 of Sequence ID Nos: 1-11. Residue 25 in this example corresponds to residue 13 of Sequence ID Nos: 1-11. Residue 48 below corresponds to residue 38 of Sequence ID Nos: 1-11. Residue 124 in this example corresponds to residue 104 of Sequence ID Nos: 1-11.

Plasmid Construction.

The expression vector for mSA was constructed by cloning the mSA gene (FIG. 6a) downstream of the outer membrane protein A (OmpA) signal sequence in pET32, a low copy number expression vector that helps keep the rate of protein synthesis low and optimize periplasmic expression. The OmpA signal peptide (MKKTAIAIAVALAGFAT-VAQA—SEQ ID NO: 12) was followed by the SpeI restriction enzyme recognition sequence and a 6×His tag, which was in turn followed by two restriction sites for EcoRI and NheI. mSA was cloned using NheI and BamHI and was followed by the FLAG epitope tag (DYDDDDK (SEQ ID NO: 13)-Stop) and a XhoI site. The resulting expression vector was named pET32-OmpA-mSA (FIG. 6b).

Expression and Purification of Recombinant Fusions.

pET32-OmpA-mSA was introduced into BL21(DE3) pLysS and the cells were plated on (Luria Bertani) LB agar containing ampicillin. Several colonies were picked from the plate to initiate an overnight LB starter culture containing 200 μg/ml ampicillin, 1% glucose and 50 μg/ml chloramphenicol. Terrific Broth (TB) (microbial growth medium) powder was mixed with biotin powder. Both powders were dissolved in water. Biotin was added to the culture mix prior to autoclaving to ensure that it was fully dissolved by the time the cells we-re added. Raw biotin powder must be added rather than a stock solution of biotin in dimethyl sulfoxide (DMSO), since DMSO can affect cell growth, even at low concentrations. Glucose, glycerol and α-lactose were combined to prepare a 50× stock solution in water, termed 5052, and autoclaved separately. Glucose was added to the medium to repress potential leaky expression that can affect cell viability and lead to lower final protein yields. MgSO$_4$ was prepared as a 500× stock in water and autoclaved separately. One or more of the components in 5052/MgSO$_4$ were seen to precipitate when heated with TB so these stocks were added after everything has cooled to room temperature. All solutions were combined and ampicillin was added to form TB supplemented with 0.05% glucose, 0.5% glycerol, 0.2% α-lactose, 1 mM MgSO$_4$, 900 μM biotin, and 200 μg/ml ampicillin. The composition of Terrific Broth is well known. For example, the composition can be tryptone (pancreatic digest of casein) 12 g/L, yeast extract 24 g/L, K$_2$HPO$_4$ 9.4 g/L (dipotassium phosphate), KH$_2$PO$_4$ 2.2 g/L (monopotassium phosphate).

The following morning, the starter culture was diluted 100 fold into the supplemented TB. The cells were grown at 37° C. and 300 rpm until OD$_{600}$=0.3, at which point the shaker temperature was reduced to 20° C. Active cooling in water was used for a large culture volume. Once the culture had reached OD$_{600}$=0.6, IPTG was added to the final concentration of 75 μM and the shaker speed was increased to 375 rpm. Shaking the cells until they are partially lysed (which can be monitored based on increasing viscosity of the medium) is important to make the protein in abundance. If the medium is "not" viscous, this means the cells did not lyse during induction (e.g. the shaking was not vigorous enough), and when this happens, there is very little mSA in the medium.

Following 24 hr induction at 20° C., cells were removed by centrifugation and the culture medium was collected for purification. Since the viscosity of our culture medium increased during induction (possibly due to partial lysis of the cells), the medium was sonicated with a 200 W sonicator (30 sec on, 30 sec off for 4 cycles at 50% amplitude capacity). Theoretically, the medium should have the same consistency and viscosity as the original growth medium before cell growth. However, this is not the case, because the cells die during induction due to shaking, etc, and release their contents to the medium. Bacterial DNA that is released to the medium following cell lysis makes the medium noticeably viscous. Sonication shears DNA into smaller pieces and restores the original viscosity. Sonication before purification affects the yield by many folds. The pH of the culture medium was adjusted to 7.5 with NaOH, and imidazole was added to 10 mM. The medium was centrifuged at 12,000 rpm to remove any precipitates that may have formed during the work-up. The clarified medium was passed through a column packed with Ni-NTA Superflow Agarose pre-equilibrated with PBS and 10 mM imidazole. The column was washed with PBS and 20 mM imidazole and the bound protein was eluted in a single step with 300 mM imidazole in PBS. The eluted protein was concentrated using a centrifugal filter (Amicon) with the nominal cutoff of 10 kDa, and buffer exchanged to 100 mM glycine buffer pH 2.3 to remove bound biotin. Finally, the sample was buffer exchanged back to PBS. The yield was estimated based on A$_{280}$ measurements with the predicted extinction coefficient ε=37,530 M$^{-1}$ cm$^{-1}$ and purity was assessed by SDS-PAGE with Coomassie staining.

The purification of thioredoxin-mSA was carried out as previously described (Demonte et al., 2014, *Appl Microbiol Biotechnol*, 98, 6285-6295). To induce thioredoxin-mSA, BL21(DE3) pLysS cells were transformed with the expression vector. Overnight LB culture containing 1% glucose was diluted 100× to inoculate LB containing 0.05% glucose. The cells were induced with 50 μM IPTG and grown 16 hr at 20° C. The cells were lysed by sonication in a buffer containing 900 μM biotin, 10% glycerol, 0.2% triton x-100, 0.2 mg/ml lysozyme, 1 mM PMSF, 10 mM imidazole, and the expressed protein was purified by immobilized metal affinity chromatography. Fused thioredoxin was removed with tobacco etch virus (TEV) protease in a buffer containing 900 μM biotin, 0.5 mM EDTA, 1.0 mM DTT. Proteolyzed mSA was purified by ion exchange chromatography.

To prepare mSA-S25R/T48F fused to EGFP, BL21(DE3) pLysS was transformed with the expression vector pRSET-mSA(RF)-EGFP. The cells were induced with 100 μM IPTG for 4 hr at 37° C. The cells were lysed in a lysis buffer containing 0.5% Triton X-100 and centrifuged. The inclusion bodies were resuspended in 6M guanidine hydrochloride and mSA(RF)-EGFP was isolated by 6×His affinity chromatography. The eluted fractions were added drop by drop to a large volume of refolding buffer containing 900 μM biotin, 1 mg/ml reduced and 0.2 mg/ml oxidized glutathione. The refolded protein was concentrated and dialyzed against tris buffered saline.

Circular Dichroism Spectroscopy.

Purified mSA was diluted to 15 μM in PBS and loaded in a quartz cuvette with 1.0 mm path length. Circular dichroism (CD) spectra were obtained using a J-715 JASCO Spectropolarimeter. The spectra were collected between 210 and 250 nm at temperatures between 20 and 90° C. in 2° C. increments. Streptavidin CD spectrum has a characteristic positive peak between 232-236 nm, which can be used to track temperature induced unfolding (Lim, et al., 2013, *Biotechnol Bioeng*, 110, 57-67). The fraction of denatured protein computed based on the value at 235 nm was plotted against temperature and fitted to the integrated form of the Van't Hoff equation to estimate the denaturation temperature.

Fluorescence Polarization Spectroscopy.

The binding of biotinylated fluorescein (bf, AnaSpec) was measured using a microplate reader (SpectraMax® i3 Microplate reader from Molecular Devices) in flat bottom 96 well plates (Sterilin Ltd). To measure K$_d$, 100 nM bf was first mixed with titrating amounts of mSA in PBS containing 0.1 mg/ml bovine serum albumin (BSA). After overnight incubation at room temperature, the fluorescence polarization values were measured and fit to the quadratic binding equation (Hsu and Park, 2010, *J Mol Graph Model*, 29, 295-308). To measure the off rate (k$_{off}$), 10 nM bf was first mixed with 50 nM mSA and incubated for 2 hr to form a biotin-mSA complex. To observe dissociation of bf, excess free biotin was added to a final concentration of 100 μM and recording of fluorescence was started immediately. The intensity of polarized fluorescence was measured at various time points and normalized with respect to the value at t=0 min. The intensities were fit to an exponentially decaying function $e^{-k_{off}*t}$ to compute k$_{off}$. The dissociation half-life t$_{1/2}$=0.693/k$_{off}$.

Labeling of Cell Surface Proteins.

Adherent HEK293 cells were seeded in a 24 well plate (Becton Dickinson) and grown in DMEM supplemented with 10% FBS and antibiotic/antimycotic (Invitrogen). At 50% confluency, the cells were transfected with a plasmid containing pDisplay-AP-CFP-TM. After 2 days the wells were supplemented with 100 nM purified BirA, 5 mM ATP, and 0.3 mM biotin and the biotinylation reaction was carried out overnight. The following morning, the cells were detached from the wells using EDTA Solution (Versene from Life Technologies), washed with PBS containing 0.1% w/v BSA (PBSF), and fixed in 4% paraformaldehyde solution. Prior to microscopy, cells were labeled with 1 µM mSA-RWT—Alexa488 or 1 µM mSA-RF—EGFP in PBSF for 30 minutes. Excess protein was washed away and cells were switched to PBSF with 0.9 mM biotin. Each sample was mounted on slides and imaged using confocal microscopy. The same field of view was imaged every 10 min for 60 min to quantify fluorescence loss as a function of time. The captured images were analyzed with microscope software (ZEN from Zeiss, and MatLab® from MathWorks).

Results.

Engineering a Binding Pocket with Reduced Solvent Accessibility.

Mutating S25 to histidine slows the dissociation rate because histidine shields the bicyclic ring of bound biotin from the bulk solvent better than smaller serine. A survey of streptavidin sequences shows that the residue corresponding to S25 varies in different homologs. The corresponding residue in bradavidin 2 (Brad2) is arginine (R17), which is involved in a hydrogen bond and a salt bridge with G105 and D106, respectively (FIG. 1a, 6a). The side chain of Brad2 R17 forms a physical barrier that blocks water molecules from entering the binding pocket. Given that L1,2, i.e. loop between 3 strand 1 and 2, adopts nearly identical conformations in mSA and Brad2, mutating S25 of mSA to arginine may similarly result in a solvent barrier in mSA to shield the binding pocket.

Brad2 also contains a phenylalanine in L3,4 that plays a similar role as W120 in wtSA by forming a hydrophobic cover to trap bound biotin (FIG. 1b). The phenylalanine lid is important for biotin binding because mutating the residue in Brad2 to alanine reduces the biotin affinity of the protein. Dimeric shwanavidin also contains a functionally important phenylalanine at the same position, indicating that both proteins use a common mechanism to stabilize the bound ligand. The mSA residue corresponding to the phenylalanine is T48, which is likely too small to create a fully hydrophobic binding pocket. We mutated T48 of mSA to phenylalanine to check if this would improve its biotin binding by forming a hydrophobic lid. Together, modeling suggested that the dissociation kinetics are improved through targeted mutations at S25 and T48.

Extracellular Secretion Using the OmpA Signal Sequence.

Figure 2:
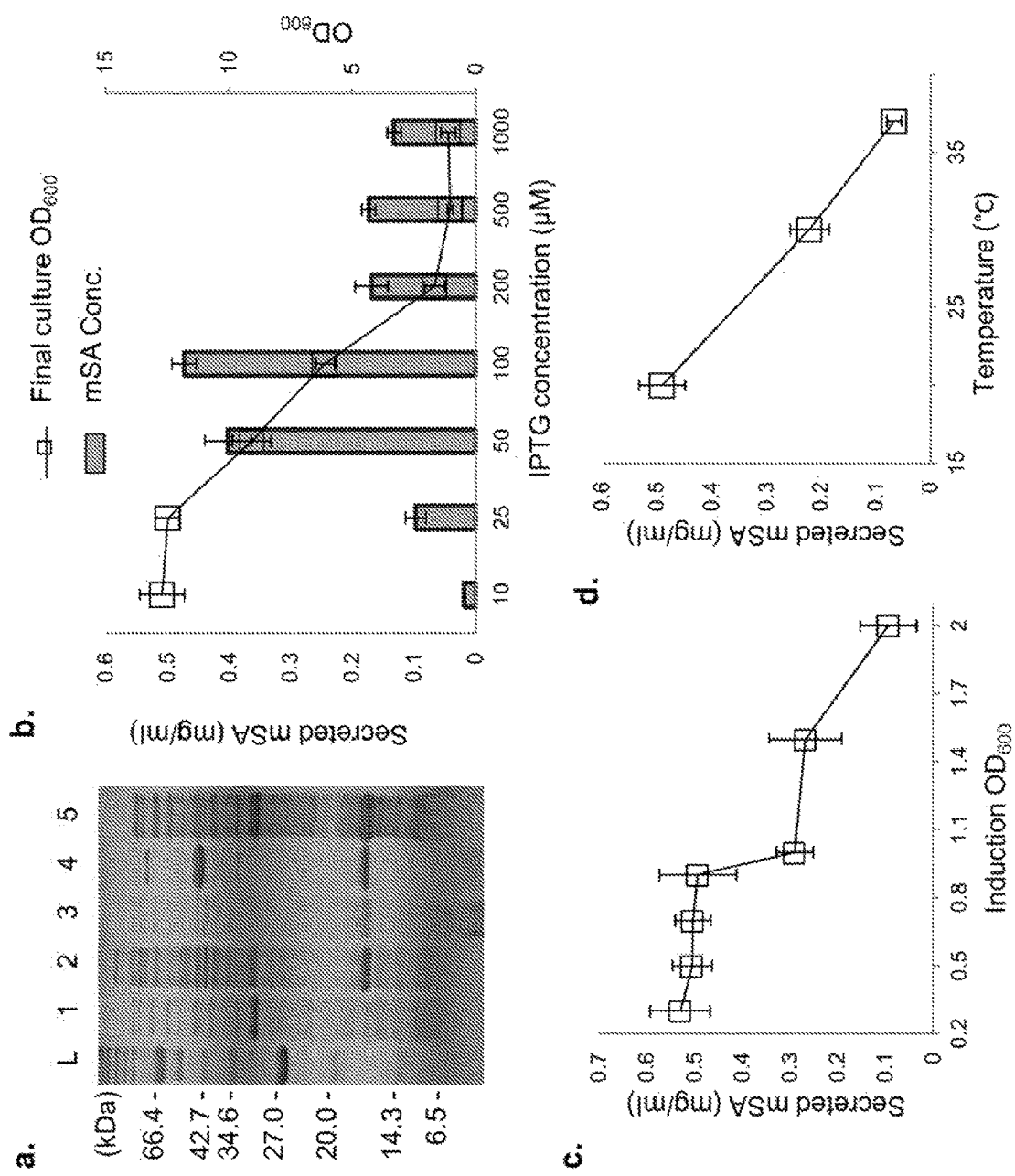
FIG. 2. Optimization of mSA secretion. a) Expression and purification of mSA fused to the OmpA signal peptide. L. molecular weight ladder, 1. Uninduced cells, 2. Induced cells, 3. Culture medium after induction, 4. Periplasmic fraction of induced cells, 5. Cytoplasmic fraction of induced cells. b) Amount of mSA secreted to the medium under different induction conditions (left axis). Each sample was grown in 50 ml culture and secreted mSA was purified from the culture medium by 6×His purification. The amount of secreted mSA was estimated based on UV absorption at 280 nm of purified mSA using the extinction coefficient $\varepsilon = 37,530$ $M^{-1}$ $cm^{-1}$. (right axis) Final culture density, i.e. $OD_{600}$, as a function of the IPTG concentration. c) Amount of secreted mSA as a function of the cell culture $OD_{600}$ at the start of induction. The cells were induced at 20° C. with 75 µM IPTG. d) Amount of secreted mSA as a function of the induction temperature. 75 µM IPTG was used at all temperatures.

We expressed and purified mSA mutants from *E. coli* to test if the designed mutations slow the off rate as expected. mSA expressed in the cytoplasm appears in inclusion bodies and requires folding after purification. Since inclusion body purification is lengthy and cumbersome, developing a purification method that directly expresses mSA in a functional form would simplify its preparation and thus make it easier to develop experiments based on the molecule. Past studies have shown that streptavidin homologs, including avidin, zebavidin, rhizavidin, and bradavidin, can be secreted to the periplasm using the OmpA signal peptide. We tested if mSA can be secreted to the periplasm using the OmpA signal sequence. We transformed *E. coli* with the expression vector for OmpA-mSA and induced the cells at 20° C. with 0.5 mM IPTG. An SDS-PAGE analysis shows that induced mSA is found in the cytoplasm and in the periplasmic fraction (FIG. 2a).

Surprisingly, the culture medium also contained a band with the expected mSA molecular weight, suggesting that mSA in the periplasm may be released to the medium. Since proteins in the medium are easier to purify, we optimized the induction condition to maximize mSA release to the medium. Screening the induction temperature, IPTG concentration and induction culture density showed the maximum amount of mSA is released when the cells are induced in early log phase ($OD_{600}$<0.8) at 20° C. with 50-100 µM IPTG (FIG. 2b-d). Other commonly used supplements to the culture medium had little effect on the final yield (Table 1). Table 1 shows the amount of mSA purified from the culture medium when the medium was supplemented with various additives. The cells were induced at $OD_{600}$=0.6 with 75 µM IPTG at 20° C. for 24 hr. The yields were based on purification from 50 ml cultures. After elution from Ni-NTA resin, the amount of secreted mSA was estimated based on UV absorption at 280 nm using the extinction coefficient $\varepsilon$=37,530 $M^{-1}$ $cm^{-1}$.

TABLE 1

| Additive | Additive conc. | Final mSA conc. (mg/ml) |
| --- | --- | --- |
| Terrific broth only | | 0.56 ± 0.055 |
| LB broth only | | 0.11 ± 0.031 |
| Sucrose | 0.4M | 0.58 ± 0.04 |
| Sorbitol | 0.5M | 0.59 ± 0.12 |
| Sucrose/Sorbitol | 0.4/0.5M | NDS* |
| Triton X-100 | 1% | 0.37 ± 0.061 |
| Triton X-100/glycine | 1%/2% | NDS* |
| EDTA | 34 mM | 0.12 ± 0.027 |
| DMAO | 1% | 0.37 ± 0.050 |

*No detected secretion

All the compositions in Table 1 contain 900 µM biotin.

Figure 3:
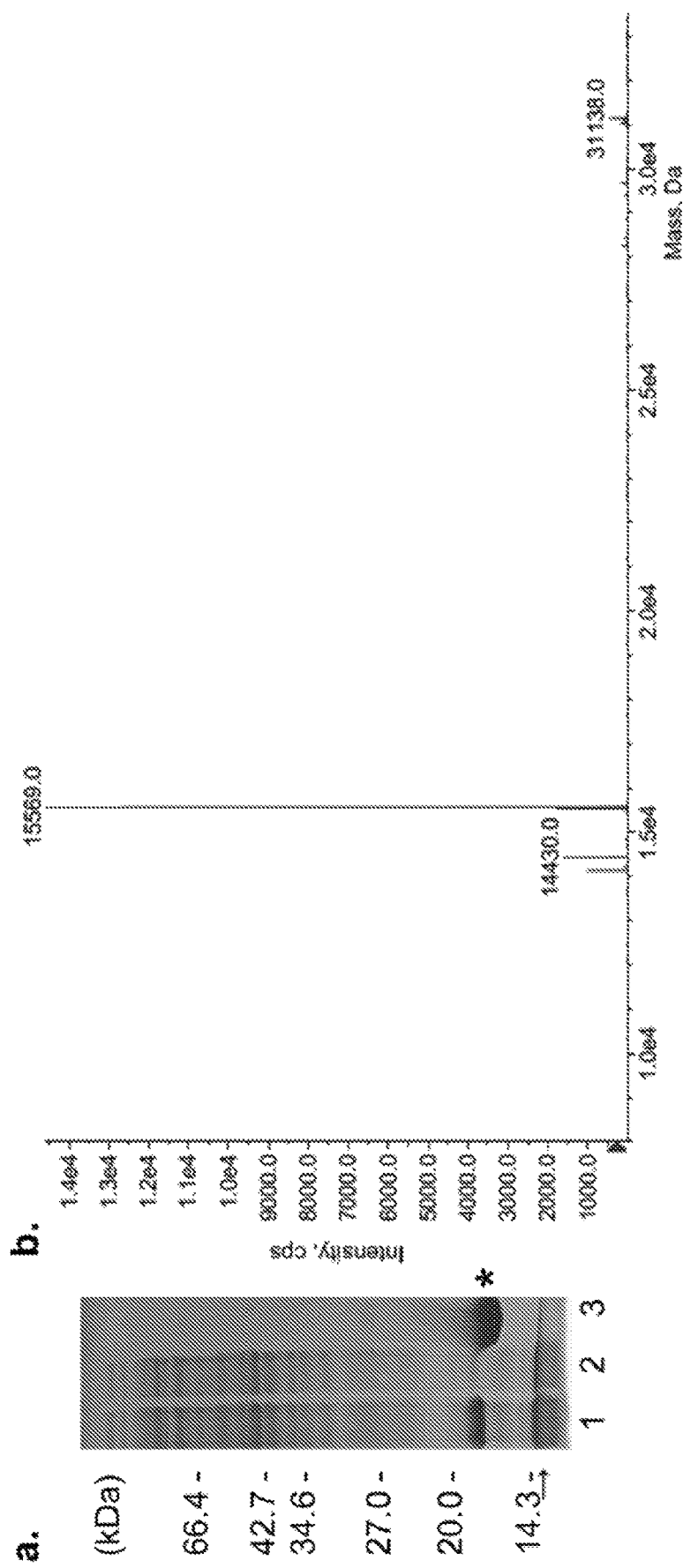
FIG. 3. Purification of mSA from the medium. a) SDS-PAGE following the purification of mSA by 6×His chromatography. 1. Culture medium at the end of induction, 2. Flow through after the culture medium has run over the Ni-NTA column, 3. Elution of bound protein with 300 mM imidazole. (→) Buffer front of the gel to show a lack of small molecular weight impurities in the eluted fraction. (*) mSA. The culture medium pH was adjusted to 7.5 before loading onto Ni-NTA resin. b) MALDI analysis of mSA-S25H purified from the medium. The major peak at 15,569 Da was consistent with the predicted MW 15,572 Da. The peak at 14,430 Da, which occurred after 3 months of storage, likely corresponds to an N-terminal cleavage product (predicted MW 14,432 Da). An intact OmpA signal peptide would have resulted in a peak of MW 17,601 Da. A minor peak corresponding to mSA-S25H dimer appears at 31,138 Da.
Figure 7:
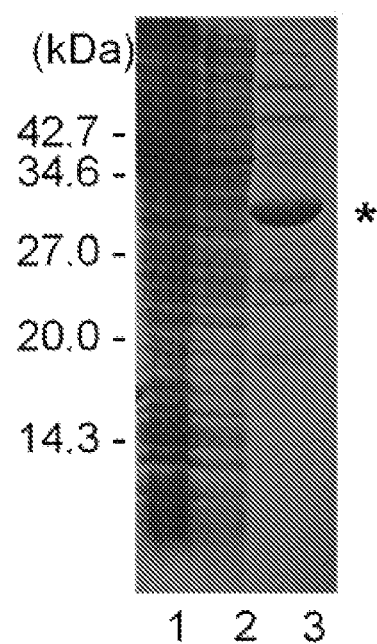
FIG. 7. Thioredoxin-mSA fusion was expressed in the cytoplasm and was purified from the cell lysate by 6×His purification as described in Demonte et al., (2014, *Appl Microbiol Biotechnol*, 98, 6285-6295) to compare with the purity of mSA isolated from the culture medium. 1. Flow through after the cell lysate has run over Ni-NTA, 2. Wash of the Ni-NTA column, 3. Elution of bound protein with 300 mM imidazole. (*) Thioredoxin-mSA. A number of impurities were seen in the eluted sample that were not present in the mSA purified from the medium. See FIG. 3a, lane 3.

We purified secreted mSA from the culture medium using the 6xHis tag fused at the N-terminus. Following elution from the resin, the purity of the protein was analyzed by SDS-PAGE and Coomassie staining, which showed that the protein is enriched to a high degree of purity (FIG. 3a). Furthermore, the purity of eluted protein was higher than that of intracellularly expressed thioredoxin-mSA, also purified by 6xHis affinity chromatography (FIG. 7). Since the OmpA signal peptide uses Sec-dependent secretion and results in sequence-specific proteolytic removal of the OmpA signal sequence in the periplasm, we measured the MW of purified mSA by MALDI (State University of New York, Albany). The measured MW of 15,569 Da is consistent with the expected MW of 15,572 Da for mSA without the OmpA signal sequence, which indicates the signal peptide is removed during secretion (FIG. 3b). This also confirms that mSA is released to the medium after the protein has been exported to the periplasm, rather than being indiscriminately released from the cytoplasm due to cell lysis. Some degradation of the purified protein after the N-terminal 6xHis tag was observed over time, which may be reduced by redesigning the sequence to remove a proteolysis susceptible sequence. No protein with intact OmpA signal peptide was detected based on MW measurement.

Biochemical Characterization.

Figure 4:
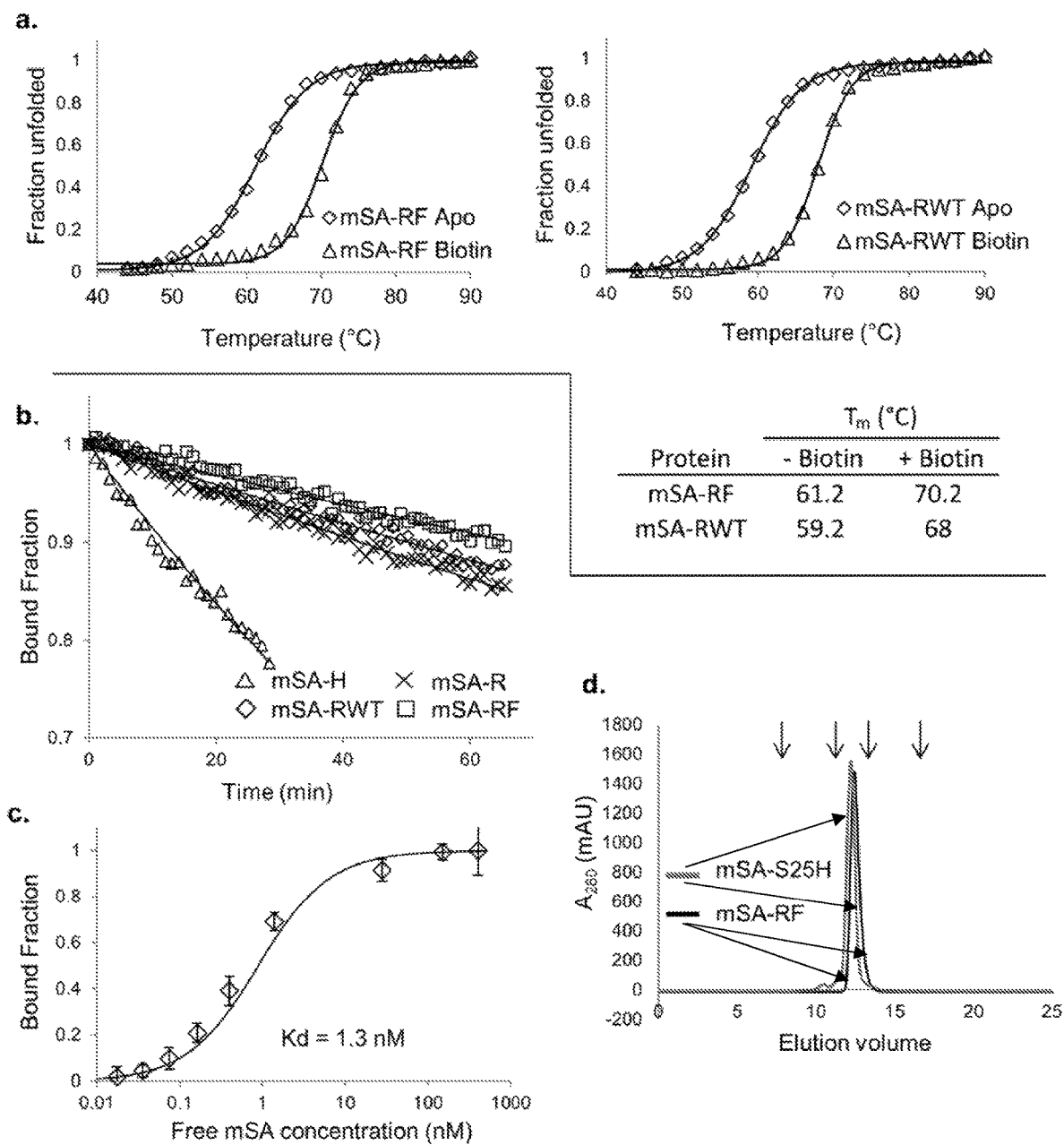
FIG. 4. In vitro characterization of purified mSA mutants. a) Stability of mSA-RF and mSA-RWT in PBS was measured by circular dichroism spectroscopy with or without biotin. b) Fluorescence polarization spectroscopy was used to measure the dissociation rate of biotin-fluorescein. The dissociation rate, $k_{off}$, was computed by fitting normalized fluorescence polarization data, or bound fraction f, to an exponentially decaying function, i.e. $f = e^{-k_{off}*t}$ The measurements were taken at 37° C. c) The equilibrium affinity of binding Kd between mSA-RF and biotin-fluorescein was measured by FP. d) mSA-S25H and mSA-RF were analyzed by size exclusion chromatography to estimate their molecular weights in solution. Each mutant eluted with a retention time that was consistent with monomeric streptavidin. The molecular weight standards (arrows) correspond to 66.0, 29.0, 12.4 and 6.5 kDa from left to right.
Figure 8:
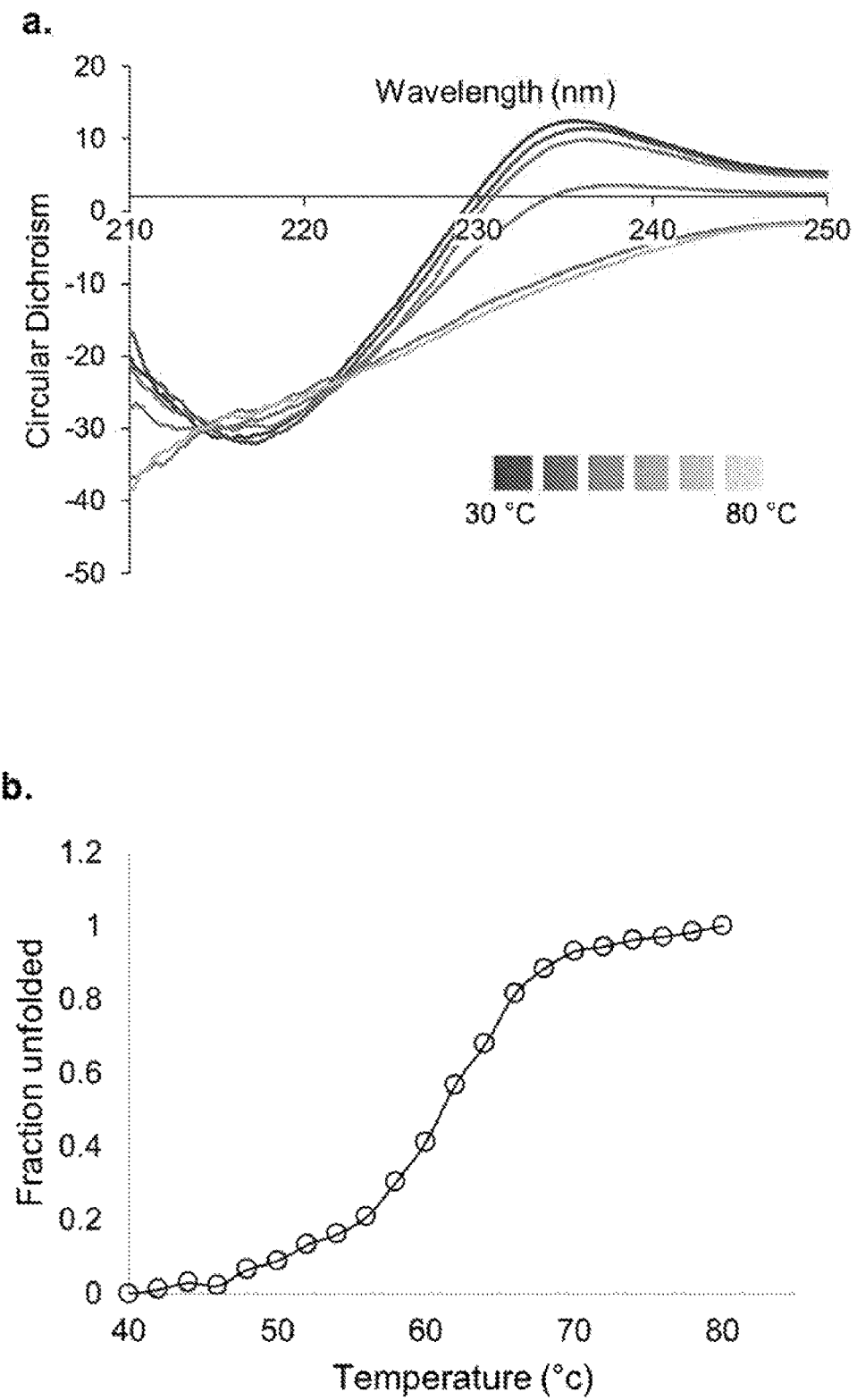
FIG. 8. Circular dichroism spectra of mSA-RF after low pH treatment to release bound biotin is shown in a). mSA-RF was first buffer exchanged to 100 mM glycine (pH 2.3) and then back to PBS (pH 7.5) before CD analysis. The spectra obtained at temperatures 30, 40, 50, 60, 70, and 80° C. were overlaid. The spectra at lower temperatures were colored darker than the spectra at higher temperatures, i.e. the darkest for 30° C. and the lightest for 80° C. The CD values at 235 nm (from FIG. 8a) were used to compute the unfolded fraction shown in b). The sharp transition from folded to unfolded at the expected denaturation temperature of 60° C. indicates that low pH treatment did not significantly affect the conformation of refolded mSA-RF.

Purified mSA (i.e. mSA-RWT and mSA-RF) undergoes a two-state transition with a midpoint of unfolding at 59-61° C. (FIG. 4a), similarly as the protein purified from the cytoplasm ((Lim et al., 2013, Biotechnol Bioeng, 110, 57-67). The denaturation temperature was higher (68-70° C.) when bound to biotin (FIG. 4a). Since mSA eluted from the resin may still contain biotin in the binding pocket, we buffer exchanged purified protein to 100 mM glycine, pH 2.3, to protonate D120 and induce dissociation of bound biotin. Although mSA may be partially or fully denatured by the low pH treatment, little to no precipitation was observed during or after the buffer exchange, indicating that mSA is stable at low pH or it can rapidly refold following denaturation. Following buffer exchange back to PBS at pH 7.5, mSA had the identical cooperative denaturation profile as the original mSA with the same temperature of unfolding, indicating that the molecule has adopted a similar native conformation (FIG. 8).

We measured the biotin dissociation rate of various mSA mutants by fluorescence polarization spectroscopy. Table 2 presents the biotin dissociation rate ($k_{off}$) of various mutants measured by fluorescence polarization spectroscopy. The S25R mutation lowered $k_{off}$ by nearly 21 fold compared to the original mSA and 3.3 fold compared to the S25H mutant (Table 2, FIG. 4b).

TABLE 2

| Protein | Residue No. | | | | $K_{off}(\times 10^{-3}\ min^{-1})$ | $t_{1/2}$ (min) |
|---|---|---|---|---|---|---|
| | 24 | 25 | 48 | 124 | | |
| | Amino acids | | | | | |
| Wt SA | | | | | 0.923 ± 0.0253 | 751 ± 261 |
| mSA | Q | S | T | E | 63 | 11 |
| mSA-H | | H | | | 8.19 ± 0.31 | 84.7 ± 3.1 |
| mSA-R | | R | | | 2.51 ± 0.11 | 277 ± 12 |
| mSA-RF | | R | F | | 1.73 ± 0.79 | 402 ± 18 |
| mSA-RWT | | R | W | T | 2.11 ± 0.13 | 329 ± 21 |
| mSA-ER | E | R | | | 10.2 ± 0.91 | 68.3 ± 6.1 |
| mSA-DR | D | R | | | 20.3 ± 0.69 | 34.1 ± 1.2 |
| mSA-ERWT | E | R | W | T | 9.73 ± 0.24 | 71.3 ± 1.7 |
| mSA-DRWT | D | R | W | T | 16.1 ± 0.52 | 43.0 ± 1.4 |
| mSA-ERF | E | R | F | | 9.15 ± 0.21 | 75.8 ± 1.8 |
| mSA-DRF | D | R | F | | 14.9 ± 0.41 | 46.7 ± 1.3 |

The S25R mutation was more effective in reducing the off rate than S25H, possibly because R25 can use its longer side chain to create a more effective solvent barrier than H25. We similarly purified the double mutant containing S25R and T48F mutations and measured its dissociation kinetics. The measured half-life of mSA-S25R/T48F (mSA-RF) was even longer ($t_{1/2}$=402 min), indicating that the two mutations function cooperatively. In contrast, the steric clashes between S25H and T48F partially offset the improvement due to S25H alone and mSA-S25H/T48F has a faster off rate than mSA-S25H. The synergy between S25R and T48F may possibly be due to the greater flexibility of arginine side chain, which allows the residue to form a solvent barrier near L1,2 while avoiding steric clashes between mutated residues. The equilibrium binding constant $K_d$ of mSA-RF ($K_d$=1.3 nM) was similar to that of mSA, indicating that the structural changes that slow the off rate of the mutant also slow its on rate (FIG. 4c).

We tested an alternative hydrophobic lid design by mutating T48 to tryptophan. The measured dissociation half-life of mSA-S25R/T48W/E124T (mSA-RWT) was likewise longer than mSA-S25R, indicating that the hydrophobic cover can be constructed using W48 as well (Table 2). To ensure that a hydrophobic mutation does not change the monomeric state of the molecule, we analyzed purified mSA-RF by size exclusion chromatography. The molecule migrated with mobility that was consistent with the expected size of monomeric streptavidin (FIG. 4d). Mutating Q24 to E to further approximate the binding pocket of Brad2 did not improve the dissociation kinetics. Importantly, this indicates that biotin binding cannot be predictably designed through simple grafting of residues from one protein to another (Table 2). Among the engineered mutants, mSA-RF and mSA-RWT had the slowest off rate and were therefore studied further.

Fluorescent Labeling of Cell Surface Receptors.

Figure 5:
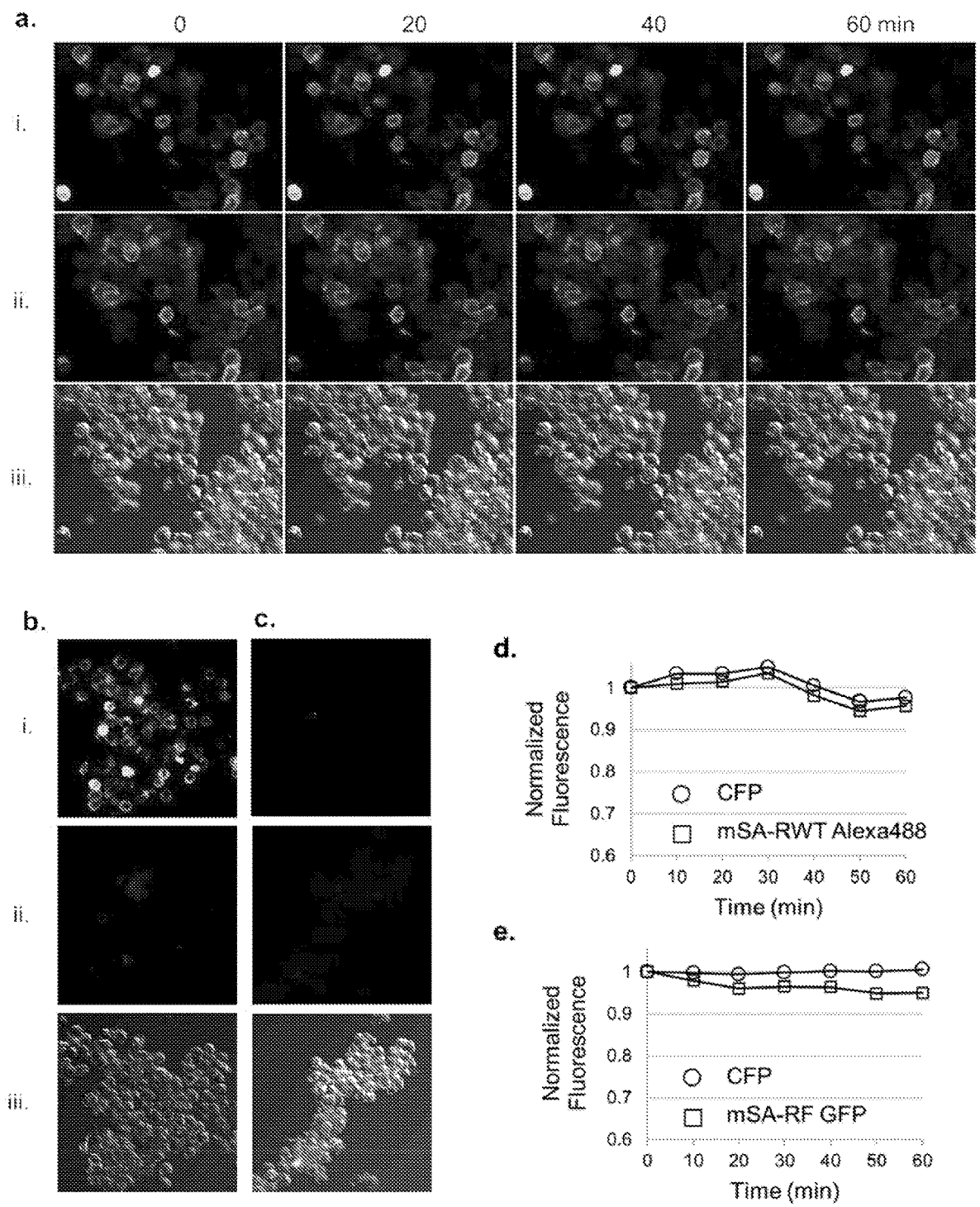
FIG. 5. Fluorescent labeling of HEK293 cells displaying biotinylated receptor. a) HEK293 cells displaying biotinylated AP-CFP were labeled with Alexa488-conjugated mSA-RWT and imaged by fluorescence microscopy. Fluorescence was filtered for (i) CFP and (ii) Alexa488 and the same field of vision was imaged multiple times at regular intervals to measure the stability of labeling. iii. DIC. mSA-RWT binds only CFP positive cells, indicating high specificity of interaction. b-c) HEK293 displaying unrelated protein fused to CFP b) or untransfected HEK293 c) were treated with purified BirA and then labeled with fluorescent mSA-RWT as in part (a) (i)-(iii) the same as before. d) The captured fluorescence images of mSA-RWT—Alexa488 labeled cells (in jpg format) were loaded into MatLab and the amount of CFP and Alexa488 fluorescence was quantified by summing over pixel values. The fluorescence intensity was normalized with respect to the value at t=0. e) Cells labeled with mSA-RF—EGFP were similarly imaged and analyzed to determine the time dependent loss of mSA labeling.

We tested the use of mSA-RWT or mSA-RF in cell imaging, in which biotinylated proteins on the cell surface were labeled with Alexa488 conjugated mSA-RWT or mSA-RF fused to EGFP, and imaged by fluorescence confocal microscopy. Cell imaging is an important test of whether engineered mutants can specifically interact with biotinylated ligands in a heterogeneous environment, in which other potentially competing interactions can interfere with desired detection. We displayed CFP fused to a biotin acceptor peptide (AP) and a transmembrane helix on HEK293 and biotinylated the displayed molecule within the AP sequence with purified E. coli biotin ligase, BirA. The cells were then fixed and labeled with fluorescent mSA-RWT or mSA-RF. Because mSA-EGFP could not be functionally secreted, the fusion was purified from inclusion bodies and folded in vitro. Only CFP positive cells were labeled selectively with fluorescent mSA-RWT or mSA-RF, indicating there is specific mSA-biotin interaction on the cell surface (FIG. 5a). The cells expressing an unrelated protein or untransfected cells were not labeled with either mSA-RWT—Alexa488 or mSA-RF—EGFP, further confirming the specificity of the interaction (FIG. 5b,c).

To evaluate the stability of labeling, we imaged the labeled cells repeatedly over 1 hr and quantified the fluorescence intensity of Alexa488 or GFP at regular intervals. Rebinding of dissociated mSA was prevented by 900 μM biotin in the labeling solution. The Alexa488/GFP fluorescence remained high after 1 hr, indicating that cell-bound mSA did not significantly dissociate during the study (FIG. 5d,e). The observed stability of bound mSA was greater than expected based on in vitro $k_{off}$ measurement. The true source of this discrepancy is not clear, but may be due to the density of expressed protein being high. Together, the current study shows that mSA-RWT and mSA-RF can interact specifically with a biotinylated model protein on the cell surface and can be used to generate stable fluorescent images of labeled cell surface proteins.

Without biotin in the culture medium the recovery of mSA was lower (about 20% of the recovery if biotin is present). This can be seen in FIG. 9a, which shows reduced recovery from the medium. FIG. 9b shows that the protein expressed without biotin does not undergo a temperature-induced two state transition, i.e. it doesn't unfold cooperatively, which suggests misfolding. It was also observed that if the mSAs are isolated from the culture medium without biotin, they do not fold properly and are unable to bind biotinylated ligands. Thus, biotin in the culture medium not only helps in improving recovery of mSA, but also helps with its proper folding such that it can bind biotinylated ligands.

DISCUSSION

The Off Rate was Improved by Mutations that Shield the Binding Pocket.

Oligomerization plays an essential role in streptavidin for high affinity biotin binding by allowing W120 of a neighboring subunit to form a "hydrophobic lid" over bound biotin. However, Brad2 can bind biotin with $K_d$<0.1 nM while remaining a monomer at low pH and protein concentrations, showing that tight binding can also be achieved without oligomerization. In Brad2, F42 serves a functionally similar role to streptavidin W120 and is used as a lid to limit solvent access to the binding pocket. However, when we previously measured the dissociation rate of a mutant mSA containing T48F mutation, it was nearly identical to that of mSA (Demonte et al., 2013, Proteins, 81, 1621-1633), suggesting that the mutation alone is not sufficient to slow the rate of complex dissociation. For example, the F48 lid contacts biotin at its methylene groups but does not shield the bicyclic ring involved in streptavidin hydrogen bonds. In contrast, the single mutation S25R improved the off rate by 25 fold ($t_{1/2}$ from 11 min to 277 min). Therefore, limiting solvent access near L1,2 was helpful in slowing the dissociation kinetics.

T48F synergizes with S25R and the double mutant binds biotin more stably (i.e. slower off rate) than the corresponding single point mutants, i.e. S25R or T48F. On the other hand, both T48F and T48W diminish the off rate enhancement from S25H, indicating that these mutations do not synergize. These different outcomes could be related to structural differences between histidine and arginine, including their shape and flexibility, which may affect their interaction with T48F and T48W. The improvement in the dissociation rate from S25R and T48F (or T48W) is partially lost when Q24 is mutated to D or E (Table 2), although the corresponding residue in Brad2 is glutamate. Therefore, simply replacing the binding site residues of mSA with corresponding residues in Brad2 does not always improve its biotin binding properties. The acceleration of biotin dissociation by a negative charge near the binding pocket is consistent with the slowing of the off rate following E124T, and suggests a role of electrostatic repulsion in the dissociation process.

Although streptavidin homologs have been functionally expressed in E. coli by secreting to the periplasm, the reported yield, e.g. 10 mg/L for avidin, is much lower than the values we observe for mSA (e.g. 500 mg/L for mSA-S25H), suggesting that the monomeric structure of mSA variants facilitates their expression in bacteria. To optimize the yield of functional mSA, it is essential to supplement the culture medium with biotin. Several pieces of evidence suggest that mSA prepared without biotin is misfolded and lacks the disulfide bond. For example, when the cells were induced without biotin, the culture medium containing secreted mSA caused an immediate color change of Ni-NTA from light blue to brown (data not shown), as often observed in the presence of β-mercaptoethanol or DTT (FIG. 9a). This is consistent with the nickel atoms being reduced by the sulfhydryl groups of cysteine side chains and suggests the cysteines of mSA do not form a disulfide bond. Furthermore, mSA purified from a medium lacking biotin does not undergo a two state transition from folded to unfolded, as expected of a well folded protein (FIG. 9b). Finally, the protein was prone to aggregation and precipitation when concentrated, which suggests that the conformation of the molecule was different when expressed without biotin.

In this work, we engineered streptavidin monomers with slower dissociation rates by introducing specific mutations that we considered as forming a solvent barrier and a hydrophobic lid around bound biotin. The highest fold improvement in the off rate was observed for a combination of mutations containing S25R in L1,2 and either T48F or T48W in L3,4, which increased the $t_{1/2}$ of dissociation to 5-7 hr. We also demonstrated that mSA can be purified from the culture medium by fusing the OmpA signal peptide to the protein. The new purification protocol avoids in vitro folding and is easier to implement. The engineering of mutants with slow off rates and the development of an efficient purification protocol should encourage design of novel applications based on stable, monovalent streptavidin-biotin interaction.

The preceding description provides specific examples of the present invention. Those skilled in the art will recognize that routine modifications to these embodiments can be made which are intended to be within the scope of the invention.

What is claimed is:

1. A mutant streptavidin polypeptide comprising the sequence of SEQ ID NO: 1 in which one or more of the following replacements are present:
   i). Serine (S) at position 13 (S13) to arginine (R), or lysine (K);
   ii). Threonine (T) at position 38 (T38) to phenylalanine (F), tryptophan (W), or tyrosine (Y);
   iii). Glycine (G) at position 39 (G39) to alanine (A)
   iv). Glutamic acid (E) at position 104 (E104) to threonine (T), cysteine (C), serine (S), proline (P), aspartic acid (D), glutamine (Q), leucine (L), or valine (V);
   v). Glutamine (Q) at position 12 (Q12) to Aspartic acid (D) or Glutamic acid (E); or
   vi). a combination of any of i), ii), iii), iv), and v).

2. The mutant streptavidin polypeptide of claim 1, wherein the one or more replacements are: S13 to R and T38 to F.

3. The mutant streptavidin polypeptide of claim 1, wherein the one or more replacements are: S13 to R, T38 to W, and E104 to T.

4. The mutant streptavidin polypeptide of claim 1, wherein the one or more replacements are: S13 to R.

5. The mutant streptavidin polypeptide of claim 1, wherein the one or more replacements are: S13 to R, T38 to W, and E104 to T.

6. The mutant streptavidin polypeptide of claim 1, wherein the one or more replacements are: Q12 to E, S13 to R, and T38 to F.

7. The mutant streptavidin polypeptide of claim 1, wherein the one or more replacements are: Q12 to E, S13 to R, T38 to W and E114 to T.

8. The mutant streptavidin polypeptide of claim 1, wherein the one or more replacements are: Q12 to E, and S13 to R.

9. The mutant streptavidin polypeptide of claim 1, wherein the one or more replacements are: Q12 to D, S13 to R, T38 to F.

10. The mutant streptavidin polypeptide of claim 1, wherein the one or more replacements are: Q12 to D, S13 to R, T38 to W, and E114 to T.

11. The mutant streptavidin polypeptide of claim 1, wherein the one or more replacements are: Q12 to D, and S13 to R.

12. A method of making a mutant of claim 1 comprising:
   i) introducing a vector comprising a polynucleotide sequence encoding a mutant polypeptide of claim 1 into bacteria;
   ii) growing the bacteria in a culture medium comprising from 10 µM to 1.0 mM biotin;
   iii) disrupting the bacteria to effect release of the mutant polypeptide into the culture medium, thereby allowing complexing of released mutant polypeptide with biotin;
   iv) collecting culture medium comprising the mutant polypeptide complexed with biotin;
   v) isolating the mutant polypeptide complexed with biotin from the collected culture medium; and
   vi) separating the biotin from the mutant polypeptide to obtain an isolated mutant polypeptide of claim 1.

13. The method of claim 12, wherein the culture medium comprises from 100 µM to 950 µM biotin.

14. The method of claim 13, wherein the culture medium comprises about 900 µM biotin.

15. The method of claim 12, wherein the vector further comprises a polynucleotide sequence encoding OmpA.

16. The method of claim 12, wherein separation of biotin from the mutant polypeptide to obtain isolated mutant polypeptide is carried out by exposure of the complex to:
   i) a pH of less than 3.0;
   ii) a temperature of 60° C. or higher;
   iii) multiple buffer exchanges; or
   iv) a combination of any of i), ii) and iii).

17. The method of claim 16, wherein separation of biotin from the mutant polypeptide to obtain isolated mutant polypeptide is carried out by exposure of the complex to a temperature of from 60° C. to 75° C.

18. The method of claim 16, wherein separation of biotin from the mutant polypeptide to obtain isolated mutant polypeptide is carried out by multiple buffer exchanges with phosphate buffered saline.

19. A fusion protein comprising a mutant streptavidin polypeptide of claim 1 and a second polypeptide.

20. The fusion protein of claim 19, wherein the second polypeptide is thioredoxin.

* * * * *